US012605482B2

(12) United States Patent
Hutchins et al.

(10) Patent No.: US 12,605,482 B2
(45) Date of Patent: Apr. 21, 2026

(54) SYSTEMS AND METHODS OF PREPARING AND DELIVERING OOCYST SOLUTIONS

(71) Applicant: Applied LifeSciences and Systems, LLC, Raleigh, NC (US)

(72) Inventors: James Hutchins, Raleigh, NC (US); Ramin Karimpour, Raleigh, NC (US); Elizabeth Turpin, Raleigh, NC (US); Stephen Wolfe, Raleigh, NC (US); Joshua Steven Goff, Raleigh, NC (US)

(73) Assignee: TARGAN, Inc., Raleigh, NC (US)

( * ) Notice: Subject to any disclaimer, the term of this patent is extended or adjusted under 35 U.S.C. 154(b) by 1097 days.

(21) Appl. No.: 17/258,867

(22) PCT Filed: Jul. 10, 2019

(86) PCT No.: PCT/US2019/041178
§ 371 (c)(1),
(2) Date: Jan. 8, 2021

(87) PCT Pub. No.: WO2020/018325
PCT Pub. Date: Jan. 23, 2020

(65) Prior Publication Data
US 2021/0138165 A1     May 13, 2021

Related U.S. Application Data

(60) Provisional application No. 62/696,261, filed on Jul. 10, 2018.

(51) Int. Cl.
| | |
|---|---|
| *A61L 26/00* | (2006.01) |
| *A61D 1/02* | (2006.01) |
| *A61D 7/00* | (2006.01) |
| *A61K 39/00* | (2006.01) |
| *A61K 39/002* | (2006.01) |
| *A61M 11/00* | (2006.01) |
| *A61M 11/02* | (2006.01) |
| *A61M 15/00* | (2006.01) |

(52) U.S. Cl.
CPC .......... *A61L 26/0023* (2013.01); *A61D 1/025* (2013.01); *A61D 7/00* (2013.01); *A61K 39/0003* (2013.01); *A61K 39/002* (2013.01); *A61L 26/0066* (2013.01); *A61M 11/002* (2014.02); *A61M 11/006* (2014.02); *A61M 11/02* (2013.01); *A61M 15/0005* (2014.02); *A61M 15/0066* (2014.02); *A61M 15/001* (2014.02); *A61K 2039/552* (2013.01); *A61L 2300/256* (2013.01); *A61M 2202/30* (2013.01); *A61M 2250/00* (2013.01)

(58) Field of Classification Search
None
See application file for complete search history.

(56) References Cited

U.S. PATENT DOCUMENTS

| | | | |
|---|---|---|---|
| 3,147,187 | A | 9/1964 | Edgar |
| 4,301,148 | A | 11/1981 | Shibata et al. |
| 4,863,731 | A | 9/1989 | Davis et al. |
| 5,068,104 | A | 11/1991 | Bhogal et al. |
| 6,495,146 | B1 | 12/2002 | Evans et al. |
| 7,211,265 | B2 | 5/2007 | Richards e et al. |
| 7,354,593 | B2 | 4/2008 | McDougald et al. |
| 9,050,281 | B2 | 6/2015 | Lang et al. |
| 2006/0165731 | A1 | 7/2006 | McDonald et al. |
| 2007/0026023 | A1 | 2/2007 | McDougald et al. |
| 2008/0006799 | A1 | 1/2008 | Fowle |
| 2008/0131463 | A1 | 6/2008 | Stewart-Brown et al. |
| 2008/0194006 | A1* | 8/2008 | Hutchins ................. A61P 33/02 |
| | | | 435/258.4 |

FOREIGN PATENT DOCUMENTS

| | | | |
|---|---|---|---|
| CN | 1145168 | A | 3/1997 |
| CN | 101622011 | A | 1/2010 |
| CN | 101622011 | B | 1/2010 |
| CN | 102046197 | | 5/2011 |
| EP | 0167433 | A1 | 1/1986 |
| EP | 0294941 | A1 | 12/1988 |
| EP | 1877085 | A | 1/2008 |
| EP | 2111234 | A | 10/2009 |
| WO | WO-9301276 | A1 * | 1/1993 ........... A61K 39/012 |

(Continued)

OTHER PUBLICATIONS

The Bead-Beater. https://archive-resources.coleparmer.com/Manual_pdfs/36270-02,%20-07.pdf retrieved Mar. 18, 2024.*

(Continued)

*Primary Examiner* — Oluwatosin A Ogunbiyi
(74) *Attorney, Agent, or Firm* — Williams Mullen; R. Brian Drozd

(57) ABSTRACT

The present disclosure provides systems and methods for disrupting the outer membrane of an oocyst in solution and delivering the solution to an animal. The system includes a vessel containing unbroken oocysts in solution, an oocyst processing chamber, and a delivery outlet. The unbroken oocysts are moved from the vessel through the processing chamber and a portion of the oocyst membranes are disrupted releasing sporocysts, the resulting solution is moved from the processing chamber into the delivery outlet where the solution is delivered to an animal. Methods of vaccination, including vaccination against an *Eimeria* infection, are also provided.

20 Claims, 5 Drawing Sheets

(56)                    References Cited

FOREIGN PATENT DOCUMENTS

| WO | WO-0134187 | A2 | * | 5/2001 | .............. A61P 33/02 |
| WO | 2002/037961 | A3 | | 5/2002 | |
| WO | 2009/148895 | A1 | | 12/2009 | |

OTHER PUBLICATIONS

A. Bogado et al.; "The Immunogenicity of Eimeria tennela sporozoite proteins and living oocyst vaccines in Broilers"; Semina: Ciensius Agrarias; vol. 33, Supl. 2; Oct. 2012.

R. Fetterer et al.; "Evaluation of an Experimental Irradiated Oocyst Vaccine to Protect Broiler Chicks Against Avian Coccidiosis;" Avian Diseases; vol. 58; Issue 3; Sep. 2014.

I. Anwar et al.; "Field Eval. of Eimeria Tennela gametocytes Vaccine and its comparitive efficacy with imported live vaccine LivaCox;" Parasitology Research; Dec. 2008.

M. Hafeez et al.; "Protective Effect of Egg-propogated Eimeria Tennela gameocytes as vaccine against mixed species of coccidia in chickens;" Parasitology Research; Jun. 2006.

Nov. 11, 2024 Office Action issued in Korean Patent Application No. 10-2020-7036232.

May 26, 2025 Office Action issued in European Patent Application No. 19753497.7.

* cited by examiner

SYSTEMS AND METHODS OF PREPARING AND DELIVERING OOCYST SOLUTIONS

CROSS REFERENCE TO RELATED APPLICATIONS

This application claims the benefit of U.S. Provisional Application 62/696,261 filed Jul. 10, 2018, Hutchins et al., which is hereby incorporated by reference in its entirety. The present application is related to co-pending PCT application serial number PCT/US19/41178 filed on Jul. 10, 2019 by inventor James Hutchins et al. This co-pending PCT application is incorporated herein by reference in its entirety.

1. FIELD

The present disclosure provides systems and methods for disrupting the outer membrane of an oocyst in solution and delivering the solution to an animal. The system includes a vessel containing unbroken oocysts in solution, an oocyst processing chamber, and a delivery outlet. The unbroken oocysts are moved from the vessel through the processing chamber and a portion of the oocyst membranes are disrupted releasing sporocysts, and the resulting solution is moved from the processing chamber into the delivery outlet where the solution is delivered to an animal.

2. BACKGROUND

2.1. Introduction

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present disclosure.

Vaccines are an important component of protecting humans and animals from pathogenic microorganisms, including viruses, bacteria, and parasites. Briefly, a vaccine stimulates the immune system to recognize a specific pathogen, thereby making a defense system that protects against future encounters with that microorganism in nature. Vaccines may be divided into several major classes, specifically; inactivated or killed vaccines, subunit vaccines, wildtype vaccines and attenuated or modified-live vaccines. The wildtype and attenuated vaccines give the recipient animal a mild infection. The mild infection often produces an immune response so as to prevent a greater, perhaps lethal infection from occurring in the future.

2.2. Apicomplexa, *Eimeria*, Coccidiosis, and Vaccines

Apicomplexa is a phylum of unicellular and spore forming parasites with a complex life cycle. Well-known human diseases caused by apicomplexa include babesiosis (*Babesia*), cryptosporidiosis (*Cryptosporidium parvum*), malaria (*Plasmodium*), and toxoplasmosis (*Toxoplasma gondii*). Apicomplexan diseases also effect animals and livestock. Some apicomplexa, such as *Cryptosporidium parvum* and *Toxoplasma gondii*, effect both humans and animals. Other apicomplexa such as *Eimeria* or *Theileria* only effect animals. The apicomplexa life cycle is complicated in that it has both sexual and asexual reproductive stages. The life cycle often consists of both a stage where it is excreted into the environment, and other stages that occur within the animal host. For many apicomplexa some stages of the life cycle take place in one host species and other stages take place in another host species. On the other hand, the apicomplexan parasite, *Eimeria*, is generally host specific and is monoxenous, that is the life cycle is specific for a single host species.

*Eimeria* causes coccidiosis in the wild and domesticated vertebrates such as cattle, chickens, fish, goats, pigs, rabbits, reptiles, sheep, and turkey. Different *Eimeria* species have a preferred section of the gastrointestinal (GI) tract where they reproduce and cause damage to the epithelium of the GI tract.

Portions of the life cycle of an *Eimeria* oocyst whether wildtype or attenuated are illustrated in FIG. 1A & FIG. 1B. FIG. 1A portrays an overview of the external process that occurs with *Eimeria* oocyst uptake in chickens. The day-of-hatch chicken is first inoculated with vaccine that contains sporulated oocysts (A). The sporulated oocyst is then processed within the digestive tract of the chicken, this process is shown in greater detail in FIG. 1B. The infection continues through multiple life stages, eventually resulting in the formation of unsporulated oocysts that are excreted in the chicken's feces (B). Following excretion from the bird, the unsporulated oocysts are then exposed to heat, moisture and oxygen in the environment, and become sporulated over the course of several days (C). The oocysts are not infective until they are sporulated. These sporulated oocysts are then ingested by the chicken, and the cycle repeats.

FIG. 1B portrays an enlarged view of the internal processes that occur with *Eimeria* oocyst uptake in chickens. The boxed region shows a simplified depiction of the oocyst reproductive life cycle, wherein the sporulated oocyst, containing four sporocysts, is cracked, releasing sporocysts (D). Within each sporocyst are two sporozoites. Enzymatic reactions within the bird's intestines digest the endcap of the sporocyst wall (not shown), releasing the sporozoites. The motile sporozoites then seek out and infect intestinal cells (E) in different regions of the intestines in a species-specific manner. For example, in chickens *E. acervulina* infects the upper intestine, *E. maxima* infects the small intestine, and *E. tenella* infects the caecum.

Following infection of intestinal cells by sporozoites, the life cycle of the parasite continues through several stages of asexual reproduction. These cycles consist of several rounds of reproduction and amplification that result in a massive increase in *Eimeria* presence within their select regions of the intestinal tract. After amplification brought on by the asexual reproduction stages, sexual reproduction occurs and results in the production of oocysts, that will then be shed in the feces of a chicken and consumed by another chicken as depicted in FIG. 1A.

The complete process takes approximately 7 days, with exact lengths of time varying by species. The excystation process and subsequent invasion of a host cell occurs between day 0 and day 3. The asexual reproduction cycle occurs between day 3 and day 5. The sexual reproduction phase and subsequent shedding of the oocyst in the feces occurs between day 5 and day 7.

Coccidiosis is a common disease in poultry. Control of coccidiosis has typically been achieved using ionophores or chemicals in the feed. Alternative control measures are currently being sought for a variety of reasons including, but not limited to, the high cost of ionophores and chemicals, the environmental impact of ionophores and other chemicals, consumer demand for antibiotic-free poultry, and the potential for development of resistant coccidia or other resistant microbes. Vaccines for coccidiosis have the potential to drastically reduce or eliminate the need for ionophores or chemicals in feed for coccidiosis control. Vaccines are not widely used due to the lack of uniformity with mass vaccine application. As presently delivered, *Eimeria* vaccines in poultry result in inefficient first round infectivity and immunity, and typically result in a large naïve population susceptible to disease. The subsequent naïve population depend on recycling in the grow out farms to induce immunity. Output from birds infected in the first-round yield massive infection of the residual naïve population. Resolution of naivety yields high oocyst output in the period following the first-round infection, which results in susceptibility to secondary bacterial infections, such as necrotic enteritis, requiring antibiotics for resolution. Effective vaccination of all birds at the day of hatch would avoid the morbidity, mortality and lack of weight gain associated with *Eimeria* infection. See PCT Publication WO 2017/083663A1, Karimpour.

Currently the global impact of coccidiosis due to poor performance, morbidity and mortality is estimated at $300 million. In addition, an estimated $90 million is spent in the US and $3 billion globally for coccidiosis control annually.

The process of cracking open the oocyst membrane is presently thought to be facilitated by grinding of oocysts in contact with grit and feed in the gizzard of the chicken. Delivery of oocysts to unvaccinated or naïve birds at a hatchery results in inefficient vaccination, as the gut does not contain sufficient feed or grit to assist the process of cracking the oocyst wall to release sporocysts. As such, it would be preferable to deliver sporocysts directly to the day-old hatchlings as they may not have any grit or food in their digestive system to help break down the oocyst wall and release the sporocysts. Direct delivery of sporocysts to naïve birds at a hatchery can improve efficiency of vaccination, as the vaccine can be infective even in the absence of grit or food. Young chickens do have the capability of processing released sporocysts to the infected sporozoite stage in the intestines. This sporocyst vaccine strategy may prevent the need for recycling and secondary rounds of infection for the development of full immunity.

Some attempts have previously been made to crack the oocyst wall for purposes of generating a vaccine solution that is manufactured and shipped as a sporocyst vaccine. For example, others have disclosed grinding or shaking oocysts with glass beads. Additionally, European Patent 2,111,243 B1 (Hutchins et al., Embrex, Inc.) discloses methods to release sporocysts from oocysts using microchannels.

However, prior attempts to disrupt the oocyst membrane have been done in the context of preparing a solution for cryopreservation, freezing, storing, subsequent delivery, and thawing. Specifically, prior methods for producing sporocyst based vaccines have the disadvantage that the resulting sporocyst must be suspended in a cryopreservative solution and stored in liquid nitrogen long term. Such processes are well known in the art of parasitology for the preservation of master seed lines in the sporocyst form. It is also appreciated that recovery of viable sporocysts after cryopreservation is low, often only 5-10%. The real time generation and delivery of sporocysts avoids the need for cryopreservation and the resulting low recovery of viable organisms.

Another challenge is to disrupt the oocyst membrane without damaging the sporocysts. It becomes even more difficult when working with vaccines that are composed of multiple *Eimeria* species that are different sizes and have varying thicknesses and durabilities of their protective walls. Thus, the conditions needed to break the walls for a small rupture-resistant species such as *E. acervulina* may either damage previously released sporocysts or be too rigorous for a large more rupture-susceptible species like *E. maxima.*

There have been no attempts to crack the oocyst wall at the time of delivery or in an inline process where the newly released sporocysts are delivered directly and immediately to the intended recipient.

3. SUMMARY OF THE DISCLOSURE

The embodiments herein are directed to systems and methods pertaining to the in situ release of sporocysts for improved vaccination. Some embodiments described herein are directed to systems and methods for disrupting the membrane of an oocyst and delivering the membrane and its contents, viable sporocysts, to an animal.

Other embodiments described herein are directed to an oocyst solution delivered in two parts to create a gel mixture. See PCT application PCT/US2019/041178, Hutchins, filed Jul. 10, 2019.

One embodiment is directed to a method of vaccinating an animal against *Eimeria.* The method includes the steps of providing an oocyst-based solution, causing viable sporocysts to be released from oocysts, and delivering the solution containing released sporocysts to the animal.

Another embodiment is directed to a system for rupturing the outer membrane of an oocyst and subsequently delivering it to an animal in real-time. The system includes a vessel containing unbroken oocysts in solution, an oocyst processing chamber, and a delivery outlet. The unbroken oocysts are moved from the vessel through the processing chamber and a portion of the oocysts' membranes are ruptured releasing sporocysts. The resulting solution is moved from the processing chamber into the delivery outlet where the solution is delivered to an animal.

A further embodiment is directed to a method of rupturing oocysts at the time of delivery to an animal. The method includes the steps of providing a first vessel for containing a volume of unbroken oocysts in solution, a processing chamber, and a delivery device. The method further includes moving the solution of unbroken oocysts from the first vessel into the processing chamber and passing the solution through the processing chamber, whereby at least a portion of sporocysts are released into the solution. The method also includes moving the solution from the processing chamber to the delivery device where the processed solution containing released sporocysts is delivered to an animal.

Still another embodiment is directed to a system for delivering an oocyst solution to an animal.

A preferred commercial bird to be vaccinated by the method of the invention is a chicken.

A preferred composition to be administered to a chicken comprises sporocysts, or a mixture of sporocysts and oocysts, of one or more species of *Eimeria* selected from the group consisting of *E. tenella, E. acervulina, E. maxima, E. necatrix, E. mitis, E. praecox, E. hagani, E. mivati,* and *E. brunetti.*

Another preferred commercialized bird to be vaccinated by the method of the invention is a turkey. A preferred composition to be administered to a turkey comprises sporocysts, or a mixture of sporocysts and oocysts, of one or more species of *Eimeria* selected from the group consisting of *E. meleagrimitis, E. adenoeides, E. gallopavonis, E. dispersa, E. meleagridis, E. innocua,* and *E. subrotunda.*

4. BRIEF DESCRIPTION OF THE FIGURES

Having thus described various embodiments of the present disclosure in general terms, reference will now be made to the accompanying drawings, which are not drawn to scale and do not include all components of the system.

5. DETAILED DESCRIPTION OF THE DISCLOSURE

Figure 1A:
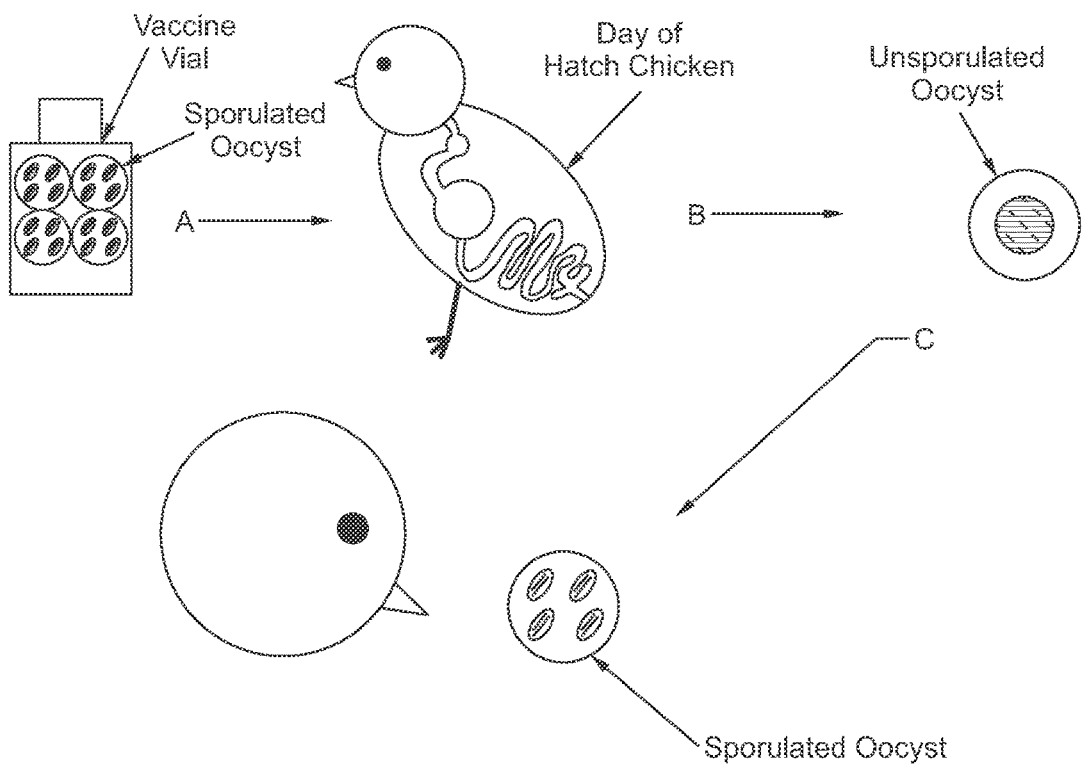
FIG. 1A is a graphic representation of the life cycle of *Eimeria* oocysts and vaccines.
Figure 1B:
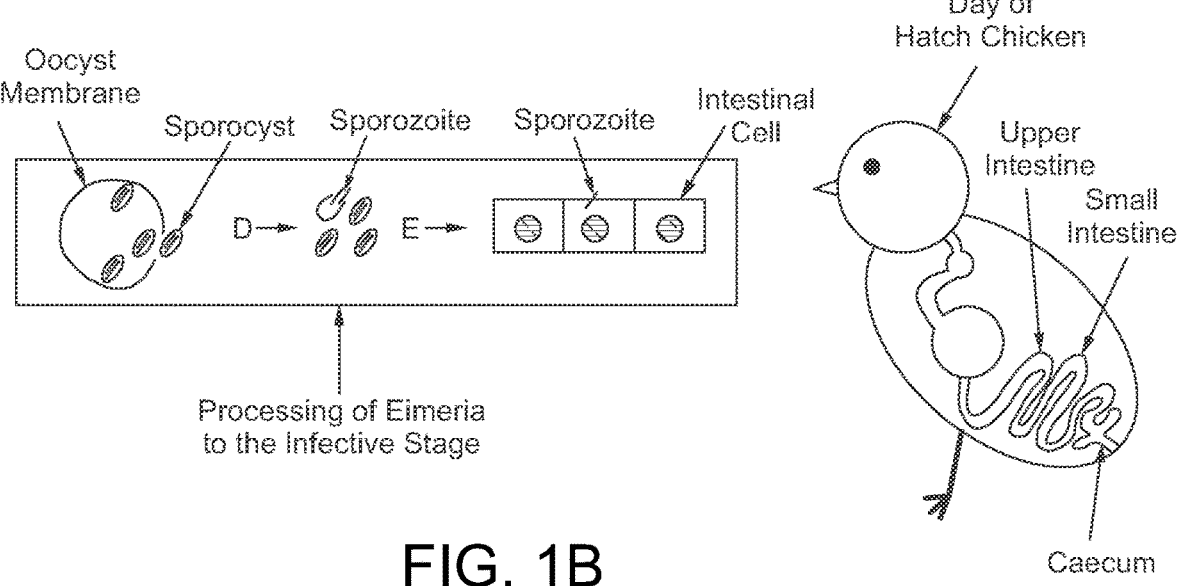
FIG. 1B is a graphic representation of the life cycle of *Eimeria* oocysts in a chicken.

Various aspects of the present disclosure will be described more fully hereinafter with reference to the accompanying drawings, in which some, but not all aspects of the disclosure are shown. Indeed, this disclosure may be embodied in many different forms and should not be construed as limited to the aspects set forth herein, rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. All publications, patent applications, patents, and other references mentioned herein are incorporated herein by reference in their entireties.

5.1. Definitions

The terminology used herein is for the purpose of describing particular embodiments only and is not intended to be limiting of the invention.

As used herein the term *Eimeria* means and includes *Eimeria* species infecting chickens consisting of *E. maxima*, *E. mitis*, *E. tenella*, *E. acervulina*, *E. brunetti*, *E. necatrix*, *E. praecox*, *E. hagani*, *E. mivati*, and any combination thereof. *Eimeria* includes species infecting turkeys such as *E. meleagrimitis*, *E. adenoeides*, *E. gallopavonis*, *E. dispersa*, *E. innocua*, *E. meleagridis*, and *E. subrotunda*, and any combination thereof. *Eimeria* also includes species infecting cattle such as *E. zuernii*, *E. bovis*, *E. ellipsoidalis*, and any combination thereof. *Eimeria* also include *E. ahsata*, *E. bakuensis*, *E. crandallis*, *E. faurei*, *E. granulosa*, *E. intricata*, *E. marsica*, *E. ovinoidalis*, *E. pallida*, *E. parva*, *E. weybridgensis*, and any combination thereof. Furthermore, the term *Eimeria* includes *E. intestinalis*, *E. vejdovskyi*, *E. piriformis*, *E. coecicola*, *E. irresidua*, *E. flavescens*, *E. exigua*, *E. magna*, *E. perforans*, *E. media*, *E. stiedae*, and any combination thereof.

The terms "animal" and "animal subjects" include but are not limited to mammalian and/or avian subjects. Suitable mammalian subjects include but are not limited to primate subjects (e.g., human subjects and non-human primate subjects such as simian), porcine, bovine (e.g., cattle), caprine, equine, feline, ovine, canine, murine (e.g., mouse, rat) and lagomorph subjects.

The terms "avian" and "avian subjects" (i.e., "bird" and "bird subjects"), as used herein, are intended to include males and females of any avian species, but are primarily intended to encompass poultry that are commercially raised for eggs, meat or as pets. Accordingly, the terms "avian" and "avian subject" are particularly intended to encompass but not be limited to chickens, turkeys, ducks, geese, quail, pheasant, parakeets, parrots, cockatoo, cockatiel, ostrich, emu and the like. In particular embodiments, the avian subject is a chicken or a turkey.

The real-time delivery of the solutions described herein means a system or method in which oocyst membranes are disrupted or otherwise broken so that the content therein is no longer contained within the oocyst membrane. The systems and methods herein are understood to be delivered within about a 24-hour period at room temperature, or within a 5-day period with refrigeration. In a hatchery, vaccine is typically introduced, stored, and delivered through a system over the course of a 4 to 8-hour shift.

As used herein, the terminology "percent reduction of oocysts" is defined as the disrupting of oocyst membranes to release internal components including sporocysts. For example, a 90% reduction in oocysts results in 10% of residual oocysts and a 90% conversion of oocysts to released sporocysts.

As used herein, the term "preening" or "preen" is defined as the act of a chicken, or other animal, ingesting oocysts, or other materials, through the act of grooming oneself, or another animal, and subsequently consuming the preened material to initiate infection.

As used herein, the term "take", "percent take", or "% take", within the context of vaccine infectivity, is defined as the subject having been shown to be positive for an apicomplexan infection, including but not limited to, *Eimeria* following vaccination.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity. The sequence of operations (or steps) is not limited to the order presented in the claims or figures unless specifically indicated otherwise.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or there below. Alternatively, depending on the context, the term "about" may mean±one half a standard deviation, ±one standard deviation, or ±two standard deviations. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

Unless defined otherwise, all technical and scientific terms used herein have the same meanings as commonly understood by one of ordinary skill in the art to which this disclosure belongs. Preferred methods, devices, and materials are described, although any methods and materials similar or equivalent to those described herein can be used in the practice or testing of the present disclosure. All references cited herein are incorporated by reference in their entirety.

5.2. Specific Embodiments

5.2.1. First Embodiment—High-Pressure Homogenization

Figure 2:
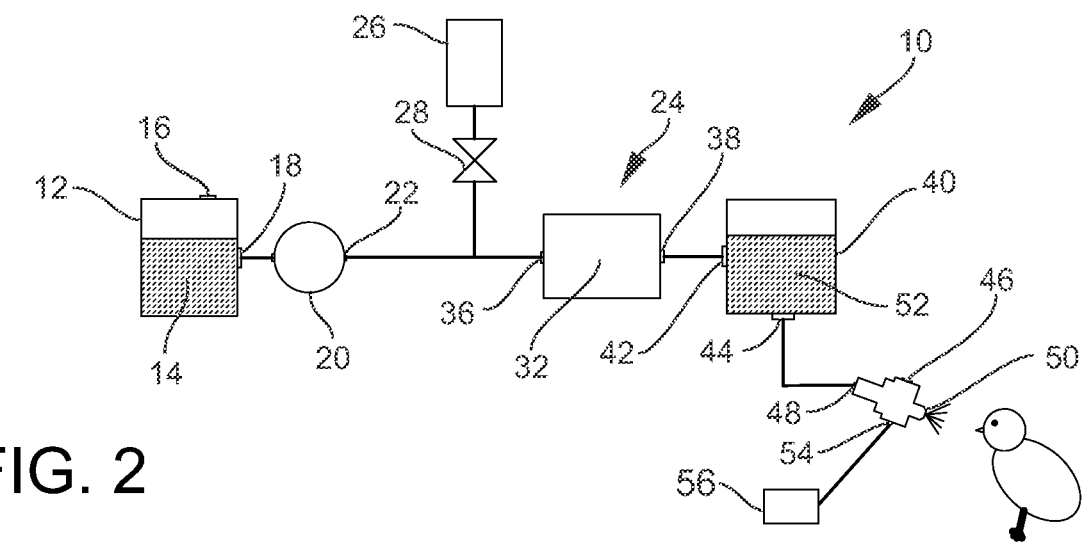
FIG. 2 is schematic drawing of the first embodiment (high-pressure homogenizer).

The first embodiment 10 is shown in FIG. 2. The first embodiment 10 includes a first reservoir 12. The first reservoir 12 is designed to hold a volume of solution 14. The solution 14 includes a vaccine (not shown) suspended in the solution. The solution 14 of the first embodiment 10 contains the *Eimeria* species oocyst-based vaccine for delivery to poultry, namely day-old hatchlings. Optionally, the solution 14 includes proteolytic enzymes. The proteolytic enzymes enable more effective uptake of the vaccine in the digestive tract of the hatchling, which will be explained in more detail below.

With regard to the solution 14, the embodiments described herein include but are not limited to *Eimeria* oocysts, and are selected from the group infecting chickens consisting of *E. maxima* oocysts, *E. mitis* oocysts, *E. tenella* oocysts, *E. acervulina* oocysts, *E. brunetti* oocysts, *E. necatrix* oocysts, *E. praecox* oocysts, *E. hagani* oocysts, *E. mivati* oocysts, and any combination thereof; *Eimeria* oocysts selected from the group infecting turkeys consisting of *E. meleagrimitis* oocysts, *E. adenoides* oocysts, *E. gallopavonis* oocysts, *E. dispersa* oocysts, *E. innocua* oocysts, *E. meleagridis* oocysts, and *E. subrotunda* oocysts, and any combination thereof *Eimeria* oocysts selected from the group infecting cattle consisting of *E. zuernii* oocysts, *E. bovis* oocysts, *E. ellipsoidalis* oocysts, and any combination thereof; *Eimeria* oocysts selected from the group consisting of *E. ahsata* oocysts, *E. bakuensis* oocysts, *E. crandallis* oocysts, *E. faurei* oocysts, *E. granulosa* oocysts, *E. intricata* oocysts, *E. marsica* oocysts, *E. ovinoidalis* oocysts, *E. pallida* oocysts, *E. parva* oocysts, *E. weybridgensis* oocysts, and any combination thereof and *Eimeria* oocysts selected from the group consisting of *E. intestinalis* oocysts, *E. vejdovskyi* oocysts, *E. piriformis* oocysts, *E. coecicola* oocysts, *E. irresidua* oocysts, *E. flavescens* oocysts, *E. exigua* oocysts, *E. magna* oocysts, *E. perforans* oocysts, *E. media* oocysts, *E. stiedae* oocysts, and any combination thereof.

The embodiments herein are directed to systems and methods for releasing sporocysts from oocysts. The oocysts can be from a protozoan that infects any animal subject, including mammalian and avian subjects.

Some embodiments described herein may also relate to methods of releasing sporozoites from protozoan oocysts. While this application focuses on *Eimeria*, some other protozoa form a life stage designated as an "oocyst" but may contain sporozoites within the oocyst and do not produce sporocysts. The embodiments may be practiced to release sporozoites from oocysts of any species of parasite that contains sporozoites within the oocyst, and would include any organisms in the phylum Apicomplexa, and would also include but not be limited to *Cryptosporidium* and *Plasmodium*. The terms "protozoa," "oocyst," "sporocyst," "sporozoite" and "merozoite" have their accepted meanings in the art. Unless indicated otherwise, these terms are intended to refer to live (i.e., viable) protozoa, oocysts, sporocysts, sporozoites and merozoites, including wildtype or attenuated forms. Also encompassed herein are genetically modified protozoa, oocysts, sporocysts, sporozoites, and merozoites.

Returning to FIG. 2 and the first embodiment 10, a first reservoir inlet 16 is fixed to the top of the first reservoir 12. The first reservoir inlet 16 receives the solution 14 into the first reservoir 12. A first reservoir outlet 18 is fixed to the first reservoir 12. The first reservoir outlet 18 is connected to a system pump 20. The pump 20 is designed to move the solution 14 from the first reservoir 12 and through the system.

Figure 3:
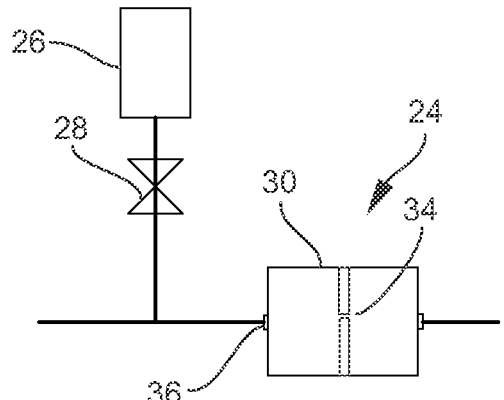
FIG. 3 is an enlarged view of the processing system of the first embodiment.

A pump outlet 22 is fixed between the pump 20 and a processing system 24. The processing system 24 of the first embodiment 10 is a high-pressure homogenizer 32. The homogenizer 32 includes a high-pressure source 26, controlled by pressure valve 28 and at least one orifice 34, shown in FIG. 3. The processing system 24 further includes a processing system outlet 38, shown in FIG. 2. The processing system outlet 38 is located within the processing system at the opposed end to the processing system inlet 36. The processing system outlet 38 is connected to a second reservoir 40 by means of a second reservoir inlet 42. The second reservoir 40 is designed to hold a volume of solution received by way of the second reservoir inlet 42.

The second reservoir 40 also includes a second reservoir outlet 44. The second reservoir outlet 44 is fluidly connected to a delivery device 46. In this first embodiment 10, the delivery device 46 is an atomized sprayer. The delivery device 46 has a delivery inlet 48, a nozzle 50 and an air inlet 54 at the nozzle 50 to atomize a plume of spray during delivery. The air inlet 54 is in fluid connection with an air pressure source 56. Alternatively, the delivery device 46 can be a hydraulic spray nozzle, or the like.

In use, the pump 20 is activated so as to move solution 14 out of the first reservoir 12 by way of the first reservoir outlet 18 and into the processing system 24 by way of the processing system inlet 36. While a pump is used to move the solution, other methods including gravity, valves, air pressure, and other methods could be used for fluid movement in any of the embodiments. High-pressure air supplied by the high-pressure homogenizer 32 is used to move solution 14 through the at least one orifice 34. The high-pressure air is over 500 psi, and preferably in the range of 500 to 6,000 psi.

As the solution 14 moves through the orifice 34 under high pressure, the oocysts are subject to shear force and the oocyst membrane will be disrupted or rupture. After the solution 14 passes through the orifice 34, it exits the homogenizer 32 through outlet 38 and moves through inlet 42 into the second reservoir 40. Each oocyst that has its membrane disrupted or rupture, will result in the release of free sporocysts into a modified solution 52. The modified solution 52 (a combination of released sporocysts and residual oocysts) is temporarily stored in the second reservoir 40 until delivery.

When the modified solution 52 is ready for delivery, the modified solution is pumped from the second reservoir 40 through the second reservoir outlet 44 and into the delivery inlet 48. The modified solution 52 is pumped into the nozzle 50 and mixed with pressurized air from the pressurized air source 56. The pressurized air atomizes the modified solution 52 at the nozzle 50 to deliver a predetermined volume of modified solution in the form of a predetermined spray profile to a specific target on an animal.

In an alternative arrangement, the high-pressure homogenizer 32 may be directly connected to the delivery device 46. In this way, the solution produced by the homogenizer 32 is delivered directly via the delivery device 46 rather than temporarily stored in the second reservoir 40.

It should be noted that the embodiments described herein relating to the disrupting of oocysts are intended to be delivered in real time. Any sporocyst-based manufactured vaccine would require a cryoprotectant formulation to maintain the viability of the sporocysts for long term storage and the implementation of a liquid nitrogen cold chain for delivery. The embodiments described herein relating to the disruption of oocyst membranes to release viable sporocysts do not require cryoprotectant solutions or any other special storage conditions such as cryopreservation.

The spray profile is directed to contact the animal at a predetermined location. The present systems are designed to target the animal's facial mucosa, particularly, the eyes or mouth. See PCT Publication WO 2017/083663A1, Karimpour. However, it is appreciated that the spray profile could be designed to target other parts of the animal's body. While it is recognized that the embodiments described herein may be applicable to all animals, the focus is on the delivery of *Eimeria* which affects poultry, particularly chicken, and more particularly, day-old hatchlings. The free sporocysts in the modified solution are able to quickly enter into the digestive tract of the hatchling. Sporocysts sprayed into the eyes, nasal passages, or mouth of the bird travel to the digestive tract. Sporocysts that are sprayed onto other parts of the bird's body such as the feathers may enter the digestive tract through preening, including self-preening and preening of other birds.

Proteolytic enzymes in the intestinal tract, including trypsin or chymotrypsin, for example, digest the Stieda body at the tip of the sporocyst allowing excystation of the infective sporozoites to occur. This enables the chick to be quickly infected by the *Eimeria* and thus develop an immune response.

It should be appreciated that the high-pressure homogenizer 24 (or other processing system described in detail below) does not have to be connected to the system, allowing for the processing to be performed off-line and delivered to container 40. The processing of the vaccine with high pressure homogenizer 24 or other systems could occur outside of the spray delivery system but in real time coincident with the preparation of the vaccine for delivery at the hatchery.

5.2.2. Second Embodiment—Bead Treatment

Figure 4:
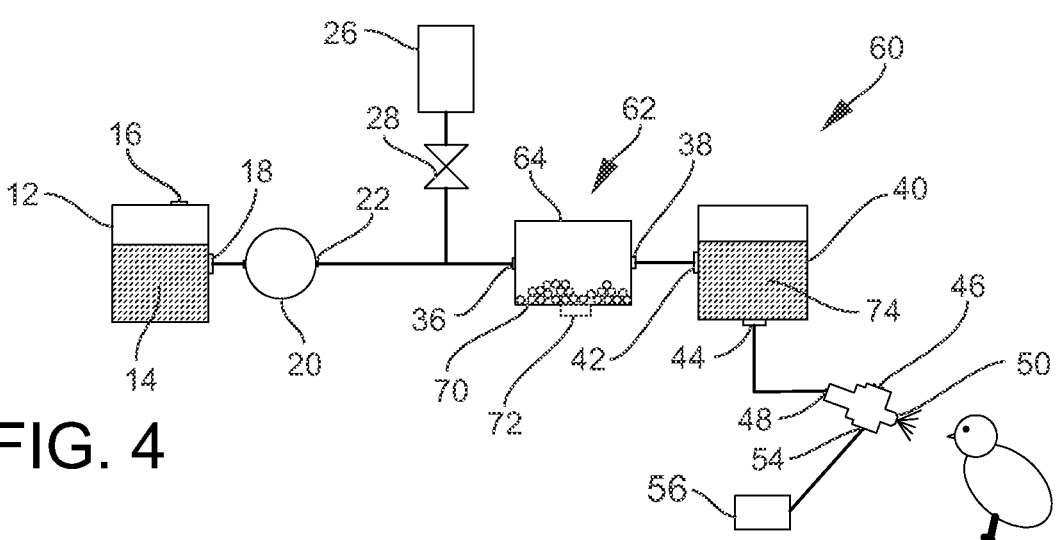
FIG. 4 is a schematic drawing of the second embodiment (bead treatment).

A second embodiment 60 of the present invention is shown in FIG. 4. Similar parts to the first embodiment 10 will be shown with similar numerical indices. The second embodiment 60 includes a first reservoir 12 having an inlet 16 and an outlet 18 and holding a volume of solution 14. The second embodiment 60 also includes a pump 20 and a pressure source 26.

The second embodiment 60 further includes a second processing system 62. The second processing system 62 includes a vessel 64 capable of holding a volume of solution 14. The vessel 64 has an inlet 36 and an outlet 38. The vessel 64 also contains a volume of agitators 70, such as glass, ceramic or metal beads or the like. It should be noted that the agitators 70 may be spherical beads, or any other shape and material that, when agitated in a volume have the capability to crush, smash or otherwise disrupt any solution contained within the volume. The vessel 64 is mounted horizontally, vertically or at some angle to enable it to rotate about its axis. The vessel 64 is connected to a spinner 72 that is capable of rotating the vessel 64 on its horizontal axis. The spinner 72 also has a vibration feature that enables it to vibrate or shake the vessel when activated. In use, the solution 14 after being exposed to the agitators in the vessel 64 results in a second modified solution 74 which will be described in more detail below.

The outlet 38 of the second processing system 62 is connected to the second reservoir 40 by means of an inlet 42. As in the first embodiment 10, the second reservoir outlet 44 is connected to the delivery device 46 where it is ultimately delivered to an animal.

The delivery device 46 includes an inlet 48 having a valve to control the flow of a second modified solution 74 into the inlet 48. It should be noted that the delivery device 46 may be altered to change the spray profile to create more or less atomization or provide a steady stream of fluid from the nozzle 50 directly to the animal.

An alternative arrangement to the second embodiment 60 is similar to the alternative arrangement described above relating to the first embodiment 10. It is envisioned that the second embodiment 60 may be designed to deliver the second modified solution 74 directly to the nozzle 50 and thus eliminate the need for the second reservoir 40.

In use, when the pump 20 and pressure source 26 are activated, the pump moves the solution 14 out of the first reservoir 12 by way of the reservoir outlet 18 and into the second processing system 62. The second processing system 62 is spun along its axis by the spinner 72. In addition, the spinner 72 causes the vessel 64 to vibrate and/or shake. The vibration and spinning cause the agitators 70 to hit and bounce off of the interior vessel walls causing at least some of the oocyst membranes in solution to be disrupted and thus release the sporocysts contained therein. The disrupted oocyst membranes and the viable sporocysts in the solution 14 create the second modified solution 74. The resulting second modified solution 74 is pumped from the vessel 64 and into the second reservoir 40 where it is temporarily held until delivery.

When it is time for delivery, the second modified solution 74 is pumped from the second reservoir 40 to the delivery device 46. The second modified solution 74 is pumped from the delivery device inlet 48 and into the nozzle 50 and mixed with pressurized air from the pressure source 56. The pressurized air atomizes the second modified solution 74 at the nozzle 50 to deliver a predetermined volume of modified solution 74 in the form of a predetermined spray profile to a specific target on an animal, in this embodiment a day-old hatchling.

In the alternative arrangement for the second embodiment 60, the second modified solution 74 is pumped directly from the vessel 64 to the nozzle 50 and to the facial mucosa of a day-old hatchling. The recently disrupted oocyst membranes and released sporocysts are ingested by the hatchling and quickly infect the digestive tract. The hatchling is able to promptly develop an immune response to the *Eimeria* and remain in good health.

5.2.3. Third Embodiment—Ultrasonication

Figure 5:
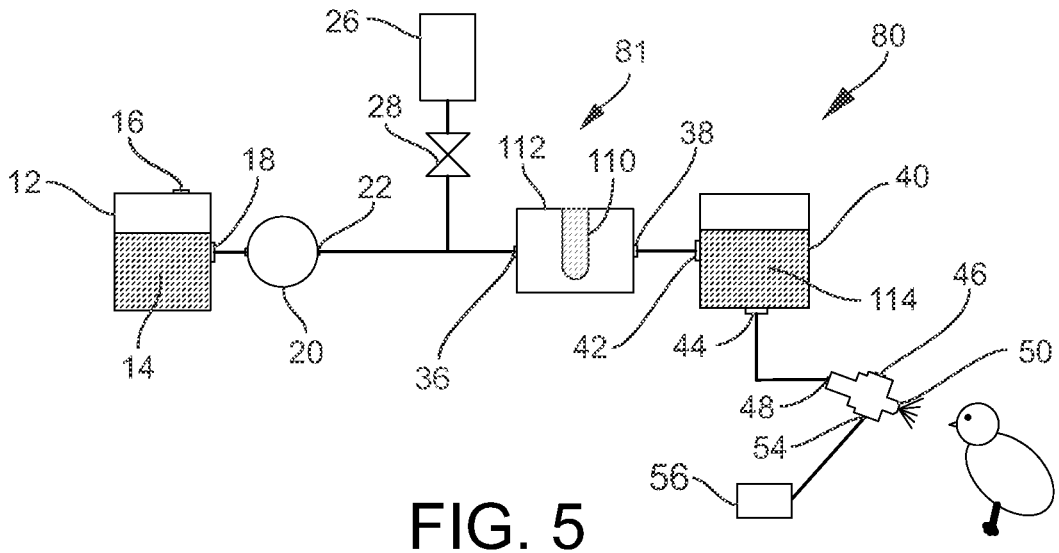
FIG. 5 is a schematic drawing of the third embodiment (sonication).

A third embodiment 80 is similar to the first 10 and second 60 embodiments described above, except for a third embodiment processing system 81. The third embodiment 80, shown in FIG. 5 includes a first reservoir 12 and pump 20. The third embodiment 80 further includes an ultrasonic probe 110 within a vessel 112. The ultrasonic probe 110 further includes a power source (not shown). Ultrasonication can occur with a probe placed directly in solution or with an indirect source placed externally to the vessel. The indirect source may be a source such sonication in a water-filled bath. The term ultrasonicator includes ultrasonic probes and indirect sources external to the vessel.

Oocysts in liquid suspension within the solution 14 are passed through the vessel 112 in close proximity to the ultrasonic probe 110 which vibrates when activated. The preferable range of vibration is between about 18 kHz to 1 MHz. The resulting energy imparted to the solution 14 yields cycles of cavitation which disrupt at least some of the oocyst membranes. The vibrational frequency and flow rate through the system are controlled such that oocyst membranes are disrupted while viable sporocysts exit the vessel 112 intact. The resulting third embodiment solution 114 is either delivered directly to the delivery device 46, such as a sprayer, or to a holding container, such as the second reservoir 40 as described above with regard to the first 10 and second 60 embodiments and alternatives thereto.

In the alternative arrangement for the third embodiment 80, the third modified solution 114 is pumped directly from the vessel 112 to the nozzle 50 and to the facial mucosa of a day-old hatchling. The recently released sporocysts and residual oocysts are ingested by the hatchling and quickly infect the digestive tract. The hatchling is able to promptly develop an immune response to the *Eimeria* and remain in good health.

A variety of commercial vendors offer sonicators with different configurations. Examples of vendors include Qsonica (Newton, CT) and Hielscher Ultrasonics GMBH (Teltow, Germany).

5.2.4. Fourth Embodiment—Rotor-Stator Mixer

Figure 6:
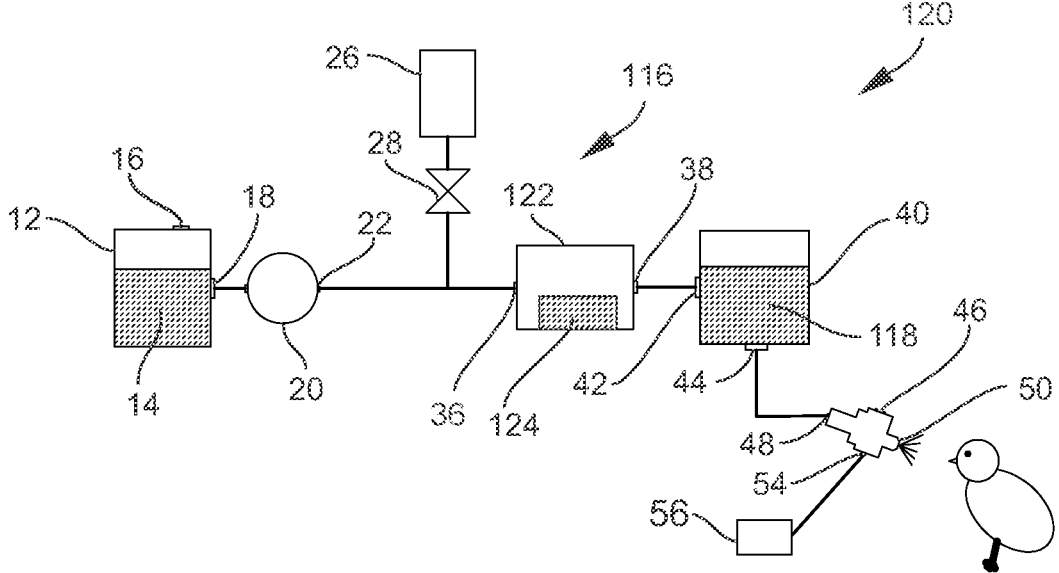
FIG. 6 is a schematic drawing of the fourth embodiment (rotor-stator mixer).

A fourth embodiment 120 uses a rotor/stator mixer processing system 116 within vessel 122 and is shown in FIG. 6. The rotor/stator mixer 116 has a dispersion head or generator 124 therein that rotates at high speed. The fourth embodiment 120 also includes a first reservoir 12, pump 20, and delivery device 46 in fluid communication with the rotor/stator mixer 116.

In use, the rotor/stator mixer 116 is activated which causes the dispersion head or generator 124 to rotate at high speed. The mixer 116 receives the solution 14 from the first reservoir 12. The solution 14 is exposed to the dispersion head or generator 124 rotating at high speed. This causes at least some of oocyst membranes to shear as a result of forces produced within the interior of the mixer 116, thus releasing at least some of the sporocysts. The resulting solution 118 is moved to the delivery device 46 where it is delivered to an animal. As discussed above, an alternative arrangement for the fourth embodiment 120 would include a second reservoir 40 to receive solution 118 which is subsequently delivered to a day-old hatchling.

5.2.5. Fifth Embodiment—Vibrating Plates

Figure 7:
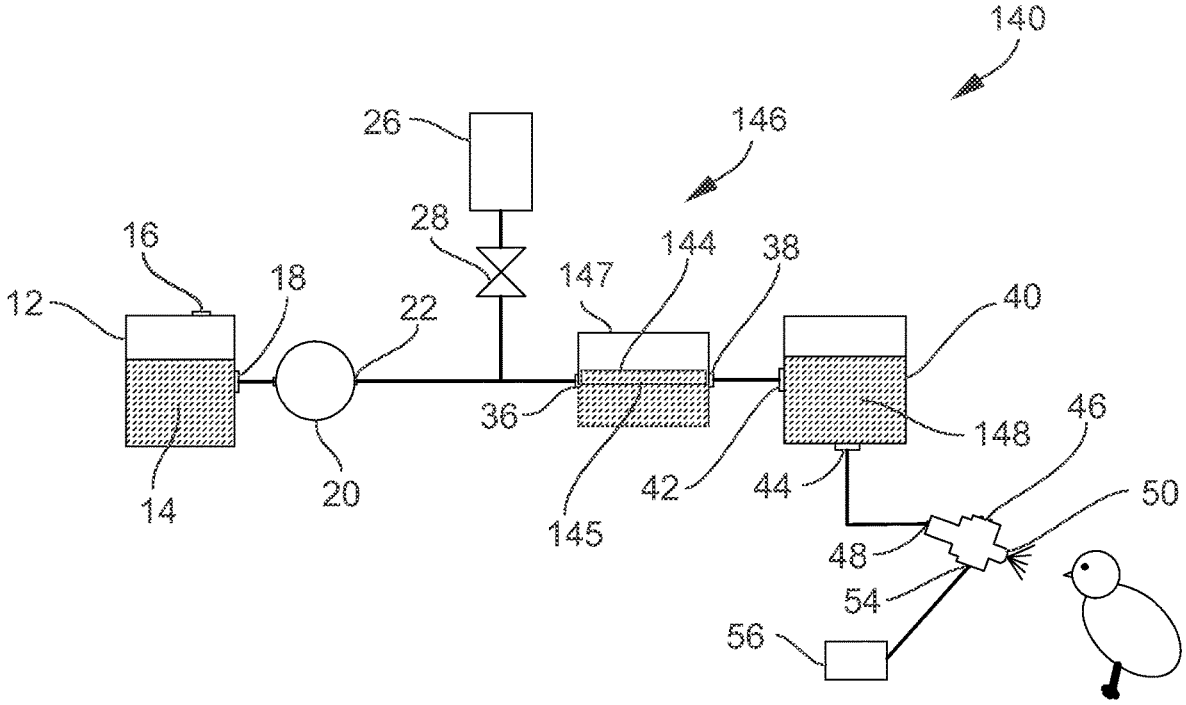
FIG. 7 is a schematic drawing of the fifth embodiment (vibrating plates).

A fifth embodiment 140 is shown in FIG. 7, and is similar to the first 10, second 60, third 80, and fourth 120 embodiments described above except for the processing system 146. The fifth embodiment 140 includes a first reservoir 12 and pump 20. The fifth embodiment 140 includes a fifth processing system 146, within containment 147, made up of a pair of plates 144, 145. The plates 144, 145 are mounted one on top of the other with some space therebetween. The first plate 144 is flat and is connected to a vibration mechanism (not shown). The vibration mechanism causes the plate 144 to vibrate. The second plate 145 may have varying degrees of smoothness or roughness as needed to disrupt the oocyst membranes during their passage between plates 144 and 145. When the plates 144, 145 are on top of each other, second plate 145 makes contact with the first plate 144.

In use, the solution 14 is moved into the fifth processing system 146. A flow of solution 14 is directed between the plates 144, 145. The vibrating mechanism is activated causing the first plate 144 to vibrate against the second plate 145. As the solution 14 moves between the plates 144, 145, at least some of the membranes of the oocysts in solution 14 are disrupted as they pass between the two plates creating a modified solution 148. The modified solution 148 is either delivered directly to the delivery device 46 or to a holding container such as a second reservoir 40.

5.3. Sixth Embodiment—Hydrodynamic Cavitation

The sixth embodiment 150 describes a process of vaporization, bubble generation and bubble implosion which occurs in a liquid as the result of a decrease and subsequent increase in local pressure. Cavitation (a phenomenon in which the rapid changes of pressure in a liquid lead to the formation of small vapor-filled cavities that can collapse when subjected to increased pressure) will occur if the pressure declines below the saturation vapor pressure of the liquid and subsequently recovers above the vapor point. This can be produced by passing a liquid through a constricted channel. The process of bubble generation, and the subsequent generation and collapse of the cavitation bubbles, results in high energy densities, and pressure on the surface of the bubbles. In initial studies, cavitation with nitrogen was explored, but any gas could be used to produce similar results. In this example, nitrogen is dissolved in the cytoplasm of the target organism (*Eimeria*) under pressure. After reaching equilibrium with the environment, the target suspension is abruptly exposed to a change in pressure resulting in nitrogen bubbles forming in the cytoplasm of the *Eimeria*. The process of intracellular bubble formation and subsequent bubble expansion causes the cellular membrane to stretch and eventually rupture. These bubbles damage the outside of the cell as a result of effervescence (escape of gas from the aqueous solution as the result of a drop in pressure that can result in the creation of foam as well as cell lysis). When tested on a multi-species oocyst suspension of *Eimeria*, lysis of the oocyst outer wall and subsequent release of the internal sporocysts was observed. This process generally occurs in a pressurized vessel. The vessel consists of a thick stainless-steel casing capable of withstanding high pressure, with an inlet for delivery of gas and an outlet port with an adjustable discharge valve.

Figures 8, 9:
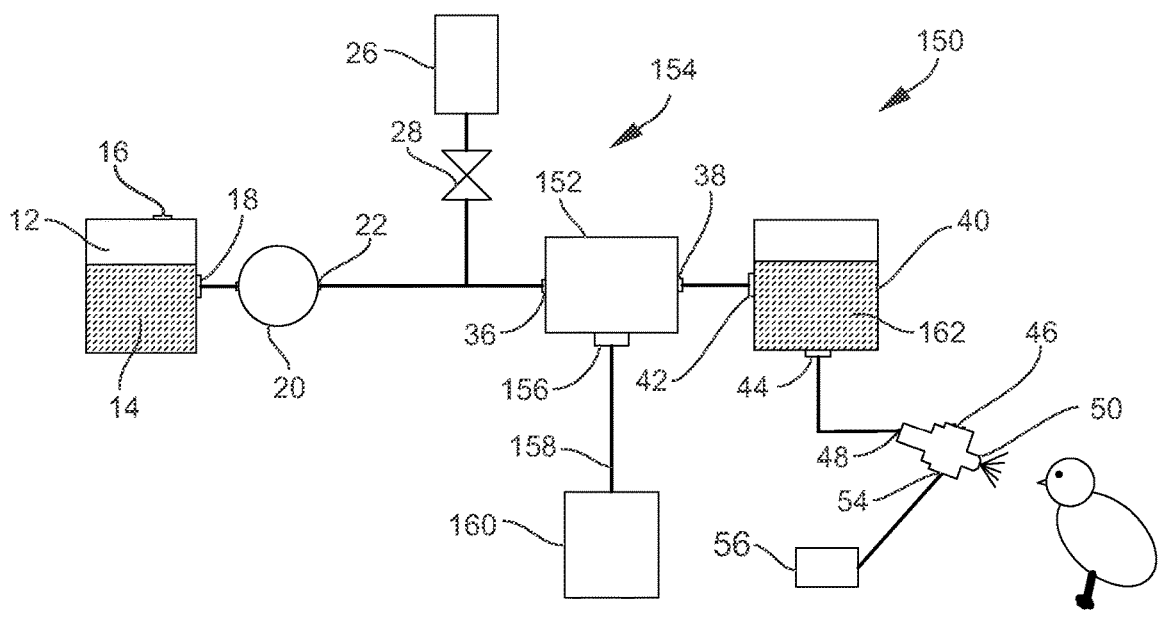
FIG. 8 is a schematic drawing for the sixth embodiment (hydrodynamic cavitation).
FIG. 9 is a schematic drawing of the seventh embodiment (high-pressure spray).

The sixth embodiment 150 is shown in FIG. 8, and is similar to the first 10, second 60, third 80, fourth 120, and fifth 140 embodiments described above except for a sixth processing system 154. The sixth embodiment 150 includes a first reservoir 12 and pump 20. The sixth embodiment 150 includes the sixth processing system 154 made up of a pressurized, metal enclosure 152, and a gas inlet valve 156. The pressurized, metal enclosure 152 is connected to a gas tank source 160 through a filling connector 158. Gas is passed through the filling connector 158 into inlet valve 156, wherein it saturates the aqueous solution present (not shown) within the metal enclosure 154. The solution enters the enclosure via inlet 36 in a manner similar to previous embodiments. Regulators (not shown) are used to control the resulting pressure from the gas flow to achieve optimal saturation.

In use, the solution 14 is moved into the sixth processing system 154. The sixth processing system 154 is then sealed and pressurized. As tank 160 releases nitrogen into the sealed pressurized tank 152, nitrogen is dissolved into the cytoplasm of the oocysts under pressure. After reaching equilibrium with the environment, the flow of nitrogen from tank 160 is ceased and the enclosure 152 is unsealed. Hydrodynamic cavitation occurs within the cytoplasm of the oocysts due to the abrupt change in pressure, causing at least some of the outer membranes to be disrupted, and allowing the internal contents, namely sporocysts, to be released. This creates modified solution 162, which is either delivered directly to the delivery device 46 or to a holding container such as a second reservoir 40.

5.4. Seventh Embodiment—High-Pressure Spray

A method for shearing oocysts and releasing intact sporocysts may include spraying a suspension of oocysts at high velocity onto a static object such that the force of impact ruptures the oocyst wall to release viable sporocysts. Additionally, a suspension of oocysts may be sprayed against a moving target, such as a spinning disk so that the combination of forces encountered shear the oocysts. The velocity of the sprayed suspension and the speed of the spinning disk may be adjusted to provide for optimization of the shearing process. The surface features of the spinning disk may be modified to produce varying degrees of smoothness or roughness as needed to shear the oocysts.

A seventh embodiment 170 is shown in FIG. 9, and is similar to the first 10, second 60, third 80, fourth 120, fifth 140, and sixth 150 embodiments described above except for the seventh processing system 172. The seventh embodiment 170 includes a first reservoir 12 and pump 20. The seventh embodiment 170 includes the seventh processing system 172 containing a nozzle 178 or other system to deliver a high-pressure spray or stream of fluid. The fluid will be released from the nozzle and impact on either a solid stationary surface, such as the wall of the vessel 174 or a spinning plate 176.

In use, the solution 14 is moved into the seventh processing system 172. A flow of solution 14 is directed through the nozzle 178. The force of the impact of the solution 14 against the wall of the vessel 174 or the spinning plate 176 will result in disrupting at least some of the oocyst membranes creating a modified solution 180. The modified solution 180 is either delivered directly to the delivery device 46 or to a holding container such as a second reservoir 40.

5.5. Additional Embodiments

It is further appreciated that while the embodiments described above often referred to pumps as a means to move solution through the system, it is envisioned that other devices such as high-pressure air and gravitational feed may also be used.

It is further appreciated that while these embodiments have focused on oocyst and sporocyst-based solutions, the solutions described herein may contain other live vaccines including those comprised of viruses, bacteria, yeast, mammalian cells, plant cells, or any genetically modified organisms. It should be apparent to one of skill in the art that solutions containing any such virus, bacteria and the like may be better suited for one embodiment over another based on the particular characteristics of the vaccine.

The system and methods described herein demonstrate that increased efficiency in vaccine response can be achieved using sporocysts, newly released from cracked oocysts and subsequently delivered by spray to initiate the *Eimeria* infection. A series of experiments using the systems and methods described above have been completed. The results are set forth below. The advantages of generating sporocyst at the time of vaccination and delivering a sporocyst-based vaccine over an oocyst-based vaccine were unexpectedly positive and yielded higher than expected responses in the recipients.

It should be appreciated that while the solution describe herein is the *Eimeria* oocyst-based vaccine, it is envisioned that there may be other oocyst-based vaccines that could also be delivered using the system and methods described herein. While preferred embodiments primarily relate to *Eimeria* vaccines for chickens and turkeys, one of ordinary skill would recognize other embodiments relating to *Eimeria* vaccines for mammals such as cattle, goats, rabbits, or sheep. Moreover, the techniques disclosed herein are useful for improved apicomplexan vaccines for any species, whether such vaccines are wildtype, or attenuated.

The systems and methods disclosed herein may be adapted for use in aquaculture. Examples of *Eimeria* which infect fish include, but are not limited to, *E. aurati, E. baueri, E. lepidosirenis, E. leucisci, E. rutili,* and *E. vanasi.* Rupturing processes may be applied to these species where applicable to facilitate release of more infective life stages for the purpose of vaccination.

It should also be noted that all embodiments described herein may be applied to an animal individually or en masse. It is appreciated that the embodiments described herein may be applied to a large group of hatchlings, or other animals, contained in a crate or other container and subject to delivery of aqueous solution. The delivery could be in the form of a two-component aqueous solution that forms a gel upon mixing. See PCT application serial number PCT/US2019/041178 filed on Jul. 10, 2019 by inventor James Hutchins.

5.6. *Eimeria* as a Vector to Deliver Recombinant Proteins

The methods and systems disclosed herein may be used with a recombinantly modified *Eimeria* to serve as vector to deliver other antigen(s). Vaccines for birds or other animals comprising disrupted cellular materials may be administered by the systems and methods described herein, including vaccines originating from viral-infected cells or vaccines originating from cell lines used to produce natural or recombinant protein products or subcellular fragments such as mammalian cells, plant cells, fungal cells, yeast cells, or bacterial cells.

Recent research demonstrates that *Eimeria* may be successfully transfected and used to express foreign antigens. It could be expected that such antigens could include viral, bacterial, or other antigens for diseases affecting poultry or other proteins or sequences to stimulate the immune system to be used singularly or in combination with antigens. In addition, antigens from other species of *Eimeria* could be expressed, allowing cross-protection for multiple species of *Eimeria* to develop from the administration of a single species of *Eimeria*. For example, Clark et al. and others have shown results demonstrating that *Eimeria* parasites can be developed as multivalent vaccine vectors and encourage the extension of these studies. See Clark et al., 2012, *Eimeria* species parasites as novel vaccine delivery vectors: Anti-*Campylobacter jejuni* protective immunity induced by *Eimeria tenella*-delivered CjaA, *Vaccine* 30(16) 2683-2688; Yan et al., 2009, Stable transfection of *Eimeria tenella*: Constitutive expression of the YFP-YFP molecule throughout the life cycle, Int'l Journal for Parasitology, 39(1) 109-117; and Marugan-Hernandez et al., 2016, Viral proteins expressed in the protozoan parasite *Eimeria tenella* are detected by the chicken immune system, Parasites & Vectors 9:463 (pub. Aug. 26, 2016, 14 pages). Similarly, *Eimeria* or other apicomplexa could be engineered as vectors to deliver other antigens to specific hosts.

The following examples further illustrate the disclosure and are not intended to limit the scope. It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

6. EXAMPLES

6.1. Gavage (Oocysts vs. Sporocysts)

Oral gavage, delivery via the mouth, is believed to be the gold standard for delivery of oocysts to a bird. In studies using a commercial broiler vaccine, results with oral gavage were found to be more variable than anticipated. Specifically, the results below indicated that infectivity from oocysts delivered by gavage varied greatly by *Eimeria* species and across test dates. This observation led us to test administration to the eyes (eyedrop) as an alternative delivery means for a positive control. In addition, disrupting the oocysts to release the sporocysts was found to be more effective when delivered via gavage. Oocyst membrane disruption was accomplished via shaking a multi-species oocyst suspension with 4 mm glass beads by a manual process. It may be hypothesized that the day-old hatchlings need feed in their crop to crack the oocysts. In experimental settings and in normal hatchery settings, the hatchlings do not receive food for 3-8 hours due to storage and transportation, allowing the oocysts to pass though the intestinal track unprocessed. Vaccination via eyedrop may slow the movement of the oocysts reaching the gut and could expose the oocysts to different enzymes.

The mechanical disruption of oocyst membranes prior to vaccination, allows for easier processing of the sporocysts, resulting in a greater percentage of the birds being effectively vaccinated, as well as a higher level of oocyst production (output) detected on day 7. This seems to be more critical for the larger species, such as *E. maxima*, and medium species, such as *E. tenella*, than the smaller species, e.g., *E. acervulina*. The smaller species appear to be equally infective when cracked or not. The studies focused efforts on membrane disruption of the large, followed by medium oocysts. Broiler chicks were vaccinated at day of hatch with a 1× dose of commercial vaccine. Intestinal contents were collected from each bird at day 7, and oocysts enumerated via McMaster's chambers by species.

TABLE 1

| Comparison of infectivity of gavage with oocysts or sporocysts | | | | |
|---|---|---|---|---|
| | N | Percent Infected | | |
| Treatment | # birds | E. maxima | E. tenella | E. acervulina |
| Gavage Oocyst | 9 | 70% | 80% | 90% |
| Gavage Oocyst | 15 | 93% | 93% | 100% |
| Gavage Oocyst | 15 | 53% | 53% | 60% |
| Gavage Oocyst | 15 | 60% | 67% | 93% |
| Gavage Oocyst | 15 | 73% | 67% | 100% |
| Gavage Oocyst | 14 | 79% | 93% | 100% |
| Gavage Oocyst | 16 | 25% | 25% | 81% |
| Gavage Oocyst | 15 | 87% | 93% | 100% |
| Gavage Sporocyst | 15 | 100% | 100% | 100% |
| Eyedrop Oocyst | 15 | 80% | 100% | 100% |

Over time, gavage vaccination resulted in inconsistent infectivity as detected by variable results at day 7. More promising results were noted with vaccine processed to release sporocysts as well as with vaccine delivered by eyedrop.

6.2. Gavage Oocyst Vs Sporocyst

In another experiment, oocyst disruption was accomplished via shaking a multi-species oocyst suspension with 4 mm glass beads by a manual process. Enumeration of the remaining oocysts indicated conversion of approximately 64% of *E. maxima* oocysts to sporocysts, 51% of *E. tenella* oocysts to sporocysts and 17% of *E. acervulina* oocysts to sporocysts. Day of hatch chicks (15 per treatment) were inoculated with either oocyst or glass-bead-released sporocysts with residual oocysts via oral gavage and intestinal contents were collected on day 7.

TABLE 2

| Comparison of frequency and amplitude of response with gavage of oocysts or sporocysts with residual oocysts | | | | | | |
| --- | --- | --- | --- | --- | --- | --- |
| | Frequency of Response (Birds infected/Birds vaccinated) | | | Amplitude of Response (Average oocyst output per bird) | | |
| Oral Gavage Treatment | E. maxima | E. tenella | E. acervulina | E. maxima | E. tenella | E. acervulina |
| Oocysts | 13/15 (87%) | 14/15 (93%) | 15/15 (100%) | $2.30 \times 10^5$ | $4.71 \times 10^5$ | $8.94 \times 10^5$ |
| Sporocysts | 15/15 (100%) | 15/15 (100%) | 15/15 (100%) | $3.41 \times 10^5$ | $8.58 \times 10^5$ | $1.08 \times 10^6$ |
| Improvement | 13% | 7% | 0% | 1.48-fold | 1.84-fold | 1.21-fold |

The improvement shown above for frequency of response is the difference between the percentage of birds infected with the sporocysts and oocysts treatments. The improvement shown for amplitude of response is the oocyst output per bird for the sporocyst treatment divided by the oocyst output per bird for the oocyst treatment.

In this particular case, both the frequency of response and amplitude of response were increased in chicks orally vaccinated with sporocyst vaccine containing residual oocysts as compared to oocyst-based vaccine.

The variable rates of infectivity observed for gavaged birds raises questions about the effectiveness of oocyst-based vaccines administered at the hatchery. Birds administered oocyst-based vaccines at the hatchery lack the presence of food and grit in the digestive tract which may be particularly critical for processing the E. maxima oocysts to the sporocyst stage. If so, these birds would be at risk for low levels of E. maxima infectivity during the first round of infection. It would follow, then, that during the second round of infection, the largely naïve population would run the risk of extremely high infection and output rates, with additional risk of secondary bacterial infections in damaged gut tissues.

Indeed, this situation is often the case, and is one of the primary reasons some avoid vaccination and use anticoccidials and chemicals in the feed instead. The use of sporocyst-based vaccine administered by eye spray at the hatchery has the potential to markedly improve infectivity of E. maxima during the first round of infection, and thus avoid severe coccidiosis infections and risk of secondary infections during the second round of infection at a grow out facility.

6.3. Eyedrop Oocyst Vs Sporocyst

In another experiment, oocyst membrane disruption was completed via shaking a multi-species oocyst suspension with 4 mm glass beads by a manual process. Enumeration of the remaining oocysts indicated conversion of approximately 52% of E. maxima oocysts to sporocysts, 26% of E. tenella oocysts to sporocysts and 47% of E. acervulina oocysts to sporocysts. Day of hatch chicks (15 per treatment) were inoculated with either oocysts or glass-bead-released sporocysts and residual oocysts via eyedrop and intestinal contents were collected on day 7.

TABLE 3

| Comparison of frequency and amplitude of response with eyedrop administration of oocysts or sporocyst vaccine containing residual oocysts | | | | | | |
| --- | --- | --- | --- | --- | --- | --- |
| | Frequency of Response (Birds infected/Birds vaccinate) | | | Amplitude of Response (Average oocyst output per bird) | | |
| Eyedrop Treatment | E. maxima | E. tenella | E. acervulina | E. maxima | E. tenella | E. acervulina |
| Oocysts | 11/14 (79%) | 11/14 (79%) | 14/14 (100%) | $2.82 \times 10^5$ | $7.89 \times 10^4$ | $7.60 \times 10^5$ |
| Sporocysts | 15/15 (100%) | 15/15 (100%) | 15/15 (100%) | $7.14 \times 10^5$ | $3.06 \times 10^5$ | $5.66 \times 10^5$ |
| Improvement | 21% | 21% | 0% | 2.5-fold | 3.9-fold | none |

It was found that the sporocyst treatment group yielded improved results in both frequency and amplitude of response for *E. maxima* and *E. tenella*. No oocysts were observed in the intestinal contents of the untreated control birds.

6.4. Delivery of Sporocysts by Spray

In the following set of experiments, release of sporocysts was achieved by shaking a multi-species oocyst suspension with 4 mm glass beads by hand. By enumeration of the remaining oocysts, the process was calculated to have converted at a minimum 66% of large oocysts (*E. maxima* species) to sporocysts, 75% of medium oocysts (*E. tenella* species) to sporocysts, and 13% of small oocysts (*E. acervulina* and other small species) to sporocysts. Day of hatch chicks (15 per treatment) were held in a stationary position and sprayed from a device with either the untreated oocyst or glass-bead-released sporocyst treatments, as previously described above. The spray was administered through an air atomizing nozzle utilizing both liquid and air pressure aimed at the facial mucosa of the chick. The birds were then given access to food and water, grown for 7 days and then sacrificed to collect each bird's intestinal contents. Below are the data tables associated with these respective spray vaccination experiments.

TABLE 4

Frequency and amplitude of response for birds sprayed with oocysts or sporocysts for Study A

| Treatment | Frequency of Response (Birds infected/Birds vaccinated) | | | Amplitude of Response (Average oocyst output per bird) | | |
|---|---|---|---|---|---|---|
| | *E. maxima* | *E. tenella* | *E. acervulina* | *E. maxima* | *E. tenella* | *E. acervulina* |
| Oocysts | 7/15 (47%) | 11/15 (73%) | 13/15 (87%) | $2.74 \times 10^4$ | $2.40 \times 10^4$ | $5.66 \times 10^4$ |
| Sporocysts | 14/15 (93%) | 14/15 (93%) | 15/15 (100%) | $2.55 \times 10^5$ | $1.84 \times 10^5$ | $2.9 \times 10^5$ |
| Improvement | 46% | 20% | 13% | 9.7-fold | 7.7-fold | 5.1-fold |

TABLE 5

Frequency and amplitude of response for birds sprayed with oocysts or sporocysts for Study B

| Treatment | Frequency of Response (Birds infected/Birds vaccinated) | | | Amplitude of Response (Average oocyst output per bird) | | |
|---|---|---|---|---|---|---|
| | *E. maxima* | *E. tenella* | *E. acervulina* | *E. maxima* | *E. tenella* | *E. acervulina* |
| Oocysts | 5/15 (33%) | 9/15 (60%) | 15/15 (100%) | $7.39 \times 10^4$ | $2.70 \times 10^4$ | $7.32 \times 10^4$ |
| Sporocysts | 12/15 (80%) | 13/15 (87%) | 15/15 (100%) | $1.37 \times 10^5$ | $1.46 \times 10^5$ | $1.39 \times 10^5$ |
| Improvement | 47% | 27% | 0% | 1.85-fold | 5.4-fold | 1.9-fold |

TABLE 6

Frequency and amplitude of response for birds sprayed with oocysts or sporocysts for Study C

| Spray Treatment | Frequency of Response (Birds infected/Birds vaccinated) | | | Amplitude of Response (Average oocyst output per bird) | | |
|---|---|---|---|---|---|---|
| | *E. maxima* | *E. tenella* | *E. acervulina* | *E. maxima* | *E. tenella* | *E. acervulina* |
| Oocysts | 10/15 (67%) | 11/15 (73%) | 13/15 (87%) | $1.10 \times 10^5$ | $2.27 \times 10^5$ | $1.60 \times 10^5$ |
| Sporocysts | 14/15 (93%) | 12/15 (80%) | 14/15 (93%) | $4.31 \times 10^5$ | $7.25 \times 10^5$ | $1.72 \times 10^5$ |
| Improvement | 27% | 7% | 6% | 3.9-fold | 3.2-fold | 1.1-fold |

It was found by oocyst enumeration that the frequency of infection and the amplitude of response were both improved with the sporocyst treatment.

Across all three experiments, no oocysts were observed in the intestinal contents of the untreated control birds, and positive controls, inoculated via eyedrop, yielded infectivity frequencies and amplitudes higher than those of the experimental spray treatment groups.

It should be appreciated that the results set forth in Tables 4, 5 and 6 were unexpected. The results indicate that a higher than expected uptake of the vaccine through sporocyst vaccination occurred in the chicks. This is believed to be attributed, in part, to the chick's inability to properly process unbroken oocysts in the digestive tract. The infection by sporocysts in the chicks indicates that a significant number of chicks are able to process and become infected with the sporocyst but not the oocyst. The effect is seen more for *E.*

*maxima* and *E. tenella* than with *E. acervulina*. Thus, it is believed that due to absence of abrasive material in a chick's upper digestive system, including the crop and the gizzard, the *E. maxima* and *E. tenella* oocysts are not easily broken. Sporocysts do not require abrasive material in a chick's digestive system for excystation of sporozoites. Sporocysts are easily processed to the infective sporozoite life stage by enzymes, such as proteases, in the digestive tract.

In another experiment, where birds were vaccinated in a stationary setting, grown and sacrificed at day 7 to collect intestinal contents, the effects of sporocyst versus oocyst inoculation were seen. In this case however, the chicks were sprayed with a nozzle solely utilizing liquid pressure as opposed to both liquid and air pressure. The lack of air pressure created a stream-like fluid dispense as compared to an atomized cone of vaccine. The results from this experiment can be seen in the table below.

TABLE 7

| Frequency and amplitude of response for birds sprayed with oocysts or sporocysts without air pressure | | | | | |
|---|---|---|---|---|---|
| | Frequency of Response (Birds infected/Birds vaccinated) | | | Amplitude of Response (Average oocyst output per bird) | | |
| Treatment | *E. maxima* | *E. tenella* | *E. acervulina* | *E. maxima* | *E. tenella* | *E. acervulina* |
| Oocysts | 53/60 (88%) | 58/60 (97%) | 59/60 (98%) | $1.31 \times 10^5$ | $4.37 \times 10^5$ | $4.74 \times 10^5$ |
| Sporocysts | 15/15 (100%) | 15/15 (100%) | 15/15 (100%) | $3.80 \times 10^5$ | $4.78 \times 10^5$ | $6.63 \times 10^5$ |
| Improvement | 12% | 3% | 7% | 2.91-fold | 1.09-fold | 1.40-fold |

No oocysts were observed in the intestinal contents of the untreated control birds, and positive controls, inoculated via eyedrop, yielded infectivity frequencies and amplitudes higher than those of the experimental spray treatment groups. The frequency of response and amplitude of response were numerically larger for *E. maxima* and to a lesser extent *E. tenella* and *E. acervulina*. These results indicate that regardless of the spray pattern from a nozzle, the administration of a sporocyst with residual oocyst solution yields improved results as compared to those of an oocyst solution.

In addition to manual processing of oocysts to release sporocysts, an automated process using an IKA Ultra Turrax device (IKA®-Werke GmbH & Co., Staufen, Germany) with glass beads. Glass beads were added to the vaccine volume (borosilicate glass balls, size 1-6 mm) and processed for 20-240 seconds at 4,000-8,000 rpm. Results for oocysts shearing were equivalent to manual processes with improved repeatability. Enumeration of the remaining oocyst after being processed by the IKA UTTD device indicated conversion of approximately 76% of *E. maxima* oocysts to sporocysts, 70% of *E. tenella* oocysts to sporocysts and 46% of *E. acervulina* oocysts to sporocysts. An experiment using broiler chicks with the same methodology as aforementioned yielded the following results.

TABLE 8

| Frequency and amplitude of response for birds sprayed with oocysts or sporocysts with residual oocysts processed by the IKA UTTD device | | | | | |
|---|---|---|---|---|---|
| | Frequency of Response (Birds infected/Birds vaccinated) | | | Amplitude of Response (Average oocyst output per bird) | | |
| Treatment | *E. maxima* | *E. tenella* | *E. acervulina* | *E. maxima* | *E. tenella* | *E. acervulina* |
| Oocysts | 5/15 (33%) | 4/15 (27%) | 13/15 (87%) | $2.3 \times 10^4$ | $4.16 \times 10^3$ | $8.91 \times 10^4$ |
| Sporocysts | 11/14 (79%) | 11/14 (79%) | 12/14 (86%) | $2.83 \times 10^5$ | $2.70 \times 10^5$ | $1.2 \times 10^5$ |
| Improvement | 46% | 52% | 0% | 12.3-fold | 64.8-fold | 1.2-fold |

No oocysts were observed in the intestinal contents of the untreated control birds, and positive controls, inoculated via eyedrop, yielded infectivity frequencies and amplitudes higher than those of the experimental spray treatment groups. The frequency of response and amplitude of response were numerically larger for *E. maxima* and *E. tenella*, and to a lesser extent *E. acervulina*. This data suggests that the IKA UTTD device can shear oocyst to generate a sporocyst/residual oocyst solution and provide similar results to that of hand shaking process. In yet another experiment, the differences between vaccinating with sporocyst versus oocyst can be seen. In this experiment, the release of sporocysts was achieved by shaking a multi-species oocyst suspension with 4 mm glass beads by hand. This sporocyst/residual oocyst solution and oocyst-only solution were administered to a day of hatch aimed at their facial mucosa. Two sets of nozzles were employed, with the first set administering a 2% sodium alginate solution and the second set administering vaccine in 3.0% calcium chloride solution. When these two solutions come into contact on the surface of the bird a gel is formed. The creation of gel is hypothesized to keep the oocyst/sporocyst vaccine hydrated longer as compared to a typical aqueous spray, extending the potential preening time for the birds. See PCT No. PCT/US2019/041178, Hutchins, filed Jul. 10, 2019. The results from this experiment can be seen in the table below.

TABLE 9

| | Frequency and amplitude of response for birds sprayed with oocysts or sporocysts with residual oocysts in a gel | | | | | |
|---|---|---|---|---|---|---|
| Gel Spray | Frequency of Response (Birds infected/Birds vaccinated) | | | Amplitude of Response (Average oocyst output per bird) | | |
| Treatment | *E. maxima* | *E. tenella* | *E. acervulina* | *E. maxima* | *E. tenella* | *E. acervulina* |
| Oocysts | 6/15 (40%) | 7/15 (47%) | 13/15 (87%) | $7.67 \times 10^4$ | $1.26 \times 10^5$ | $8.46 \times 10^4$ |
| Sporocysts | 15/15 (100%) | 15/15 (100%) | 15/15 (100%) | $2.51 \times 10^5$ | $4.83 \times 10^5$ | $1.90 \times 10^5$ |
| Improvement | 60% | 53% | 13% | 3.3-fold | 3.8-fold | 2.24-fold |

No oocysts were observed in the intestinal contents of the untreated control birds, and positive controls, inoculated via eyedrop, yielded infectivity frequencies and amplitudes higher than those of the experimental spray treatment groups. These results indicate that gel formulation sporocyst outperformed oocyst only in both frequency and amplitude of response. It has been noted that the infectivity of the smaller *E. acervulina* species is relatively high even if administered as oocysts rather than sporocysts. The infectivity data would indicate that *E. acervulina* oocysts can be processed to the sporocyst life stage and then to the sporozoite life stage efficiently in the digestive tract of the chicken whether feed and grit are present or not.

Gavage infectivity evidence would indicate that *E. maxima* especially may not be processed in vivo to the sporocyst stage without feed or grit being present in the digestive tract. Infectivity from *E. maxima*, and to a somewhat lesser extent, *E. tenella* is boosted by pre-processing the oocyst life stage to the sporocyst life stage prior to administration. In vitro, however, the shear force required to crack the larger *E. maxima* oocysts is much less than the shear force required to crack the smaller *E. acervulina* oocysts. (European Patent 2,111,243 B1 (Hutchins et al., Embrex, Inc.)). Therefore, a system for producing sporocyst at the point of use provides a complimentary action, combining the in vitro efficiency of cracking the larger oocyst species with the in vivo efficiency of processing the smaller oocyst species to yield more robust vaccine efficacy.

6.5. Results from a High-Pressure Homogenizer

6.5.1. Oocyst Reduction Counts—In Vitro

A liquid suspension containing oocysts of mixed *Eimeria* species was processed through a high-pressure homogenizer (HPH) IKA model 2000-4 at varying pressures. The cell suspension was loaded into the inlet of the HPH, processed at a range of pressures (200-1500 bar), and then dispensed from an outlet. The intact oocysts contained in the liquid preparation were enumerated using McMaster's floatation chambers before and after exposure to the HPH. Results are shown in the table below.

TABLE 10

| | | | | Percent oocyst reduction compared to starting material | | | |
|---|---|---|---|---|---|---|---|
| | Total Oocysts per | | | | | | |
| | Sample (Average) | | | | | | Total |
| HPH | E. maxima | E. tenella | E. acervulina | E. maxima | E. tenella | E. acervulina | Oocysts |
| Original material | $1.74 \times 10^2$ | $8.31 \times 10^1$ | $5.46 \times 10^2$ | — | — | — | — |
| 200 bar | $7.47 \times 10^1$ | $4.2 \times 10^1$ | $4.48 \times 10^2$ | 57% | 49% | 18% | 30% |
| 500 bar | $4.67 \times 10^0$ | $4.20 \times 10^1$ | $2.99 \times 10^2$ | 97% | 49% | 45% | 73% |

A comparison of residual oocyst processed at different pressures with high-pressure homogenization (HPH)

Results showed that the higher the pressure, the higher the percent oocyst reduction, and therefore the higher the percent sporocyst release was obtained.

Frequency and Amplitude of Response for Birds Sprayed with Oocysts or Sporocysts—In Vivo In this experiment birds were either exposed to a nozzle spray consisting of an oocyst solution or a sporocyst solution with residual oocysts processed by the IKA HPH 2000-4 device. The birds were then provided with food and water, grown and sacrificed at day 7 to collected individual intestinal contents. The results from this experiment are displayed in the tables below.

TABLE 11

A comparison of infectivity of unprocessed oocysts versus oocysts processed by IKA HPH 2000-4 at 200 bar

| | Frequency of Response (Birds infected/Birds sprayed) | | | Amplitude of Response (Average oocyst output per bird) | | |
|---|---|---|---|---|---|---|
| Treatment | E. maxima | E. tenella | E. acervulina | E. maxima | E. tenella | E. acervulina |
| Oocysts | 7/15 (47%) | 6/15 (40%) | 15/15 (100%) | $8.42 \times 10^4$ | $5.09 \times 10^3$ | $8.1 \times 10^4$ |
| 200 bar | 8/14 (57%) | 1/14 (7%) | 7/14 (50%) | $1.26 \times 10^4$ | $1.17 \times 10^4$ | $1.31 \times 10^4$ |
| Improvement | 10% | 0% | 0% | none | 2.29-fold | none |

TABLE 12

A comparison of infectivity of unprocessed oocysts versus oocysts processed by IKA HPH 2000-4 at 500 bar

| | Frequency of Response (Birds infected/Birds sprayed) | | | Amplitude of Response (Average oocyst output per bird) | | |
|---|---|---|---|---|---|---|
| Treatment | E. maxima | E. tenella | E. acervulina | E. maxima | E. tenella | E. acervulina |
| Oocysts | 7/15 (47%) | 6/15 (40%) | 15/15 (100%) | $8.42 \times 10^4$ | $5.09 \times 10^3$ | $8.1 \times 10^4$ |
| 500 bar | 3/15 (20%) | 7/15 (47%) | 13/15 (87%) | $2.23 \times 10^3$ | $1.05 \times 10^5$ | $3.63 \times 10^4$ |
| Improvement | 0% | 7% | 0% | none | 20.66-fold | none |

No oocysts from any species were observed in the intestinal contents of the 15 untreated control birds. The positive controls inoculated via eye drop yielded infectivity frequencies of 100% (across all species) and higher amplitudes (across all species) as compared to the experimental treatment groups. While the oocyst reduction percentages for the IKA HPH looked satisfactory from the in vitro data, it is hypothesized that the sporocysts generated from the homogenization process were also damaged, therefore resulting in poor frequency and amplitude responses in the in vivo data.

6.6. Results from a Rotor-Stator-Like Device

6.6.1. Oocyst Reduction Counts—In Vitro

A liquid oocyst suspension containing mixed *Eimeria* species was processed at varying speeds through the IKA Magic Lab, a single pass, inline, rotor-stator-like device. The cell suspension was loaded into the hopper of the Magic Lab, processed through 1-3 rotor stator generators, at varying speeds (3,000-26,000 rpm) and then dispensed from an outlet. The generators used for this experiment were the 6F model. Intact oocysts in the liquid preparation were enumerated using McMaster's floatation chambers before and after processing with the Magic Lab device. Results are shown in the table below:

TABLE 13

A comparison of residual oocysts processed at different speeds with rotor-stator

| Rotor-stator | Total Oocyst per Sample (Average) | | | Percent reduction compared to starting material | | | Total Oocyst |
|---|---|---|---|---|---|---|---|
| | *E. maxima* | *E. tenella* | *E. acervulina* | *E. maxima* | *E. tenella* | *E. acervulina* | |
| Original material | $1.86 \times 10^2$ | $8.87 \times 10^1$ | $5.22 \times 10^2$ | — | — | — | — |
| 16,000 RPM | $1.26 \times 10^2$ | $5.13 \times 10^1$ | $5.04 \times 10^2$ | 32% | 42% | 3% | 14% |
| 26,000 RPM | $1.03 \times 10^2$ | $8.4 \times 10^1$ | $5.09 \times 10^2$ | 45% | 5% | 2% | 13% |

Oocyst reduction was consistently observed for *E. maxima*, while variable reduction was observed for *E. tenella* and minimal reduction observed for *E. acervulina*.

Frequency and Amplitude of Response for Birds Sprayed with Oocysts or Sporocysts—In Vivo In this experiment, day of hatch broiler chicks were either exposed to a nozzle spray consisting of an oocyst solution or a sporocyst solution with residual oocysts processed by the IKA Magic Lab device. The birds were then provided with food and water, grown and sacrificed at day 7 to collected individual intestinal contents. The results from this experiment are displayed in the tables below.

TABLE 14

A comparison of infectivity of unprocessed oocysts versus oocysts processed by IKA Magic Lab at 16,000 rpm

| Treatment | Frequency of Response (Birds infected/Birds sprayed) | | | Amplitude of Response (Average oocyst output per bird) | | |
|---|---|---|---|---|---|---|
| | *E. maxima* | *E. tenella* | *E. acervulina* | *E. maxima* | *E. tenella* | *E. acervulina* |
| Oocysts | 7/15 (47%) | 6/15 (40%) | 15/15 (100%) | $8.42 \times 10^4$ | $5.09 \times 10^3$ | $8.1 \times 10^4$ |
| 16,000 rpm | 9/15 (60%) | 4/15 (27%) | 14/15 (93%) | $5.26 \times 10^4$ | $1.05 \times 10^3$ | $1.12 \times 10^5$ |
| Improvement | 13% | 0% | 0% | None | None | 1.47-fold |

TABLE 15

| A comparison of infectivity of unprocessed oocysts versus oocysts processed by IKA Magic Lab at 26,000 rpm | | | | | | |
|---|---|---|---|---|---|---|
| | Frequency of Response (Birds infected/Birds sprayed) | | | Amplitude of Response (Average oocyst output per bird) | | |
| Treatment | E. maxima | E. tenella | E. acervulina | E. maxima | E. tenella | E. acervulina |
| Oocysts | 7/15 (47%) | 6/15 (40%) | 15/15 (100%) | $8.42 \times 10^4$ | $5.09 \times 10^3$ | $8.1 \times 10^4$ |
| 26,000 rpm | 9/15 (60%) | 11/15 (73%) | 14/15 (93%) | $5.68 \times 10^4$ | $3.42 \times 10^5$ | $1.22 \times 10^5$ |
| Improvement | 13% | 33% | 0% | None | 67-fold | 1.51-fold |

No oocysts from any species were observed in the intestinal contents of the 15 untreated control birds. The positive controls inoculated via eye drop yielded infectivity frequencies of 100% (across all species) and higher amplitudes (across all species) as compared to the experimental treatment groups. The frequency of response was increased for *E. maxima* in both Magic Lab treatment groups however, the amplitude of response for those respective treatment groups were less than those belonging to the oocyst treatment group, but still within an acceptable range. The frequency and amplitude of response were most notably increased for *E. tenella*. These results may indicate that *E. maxima* oocysts were over processed under the conditions used.

6.7. Hydrodynamic Cavitation Experiments

6.7.1. In Vitro Studies with Hydrodynamic Cavitation

For initial testing, a low cost, leak-free reinforced aluminum whipped cream dispenser (EurKitchen EK-WHIP-18) with an attachment for a nitrogen charger and an outlet were used. The liquid containing a mixed *Eimeria* preparation was loaded into the canister, the nitrogen gas cartridge was added, and the canister was then inverted several times to allow the gas to saturate the liquid. The canister was turned upside down and the valve opened to create a pressure drop and release the liquid. The liquid preparation was counted before and after exposure to hydrodynamic cavitation to determine the percentage of oocyst disrupted by species. In some cases, the liquid was processed and released from the system, loaded back into the system, and then re-exposed to hydrodynamic cavitation two or three more times to disrupt more cells, as pressure and amount of gas could not be controlled in the initial system tests.

For the purposes of this disclosure, the act of releasing liquid that has already undergone hydrodynamic cavitation, and then reloading that same liquid back into the same vessel to be re-exposed to hydrodynamic cavitation, will be referred to as a "Pass." As such, from this point onward the terminology of "Pass 1," "Pass 2," or "Pass 3" will be used to represent the act of exposing a liquid to the process of hydrodynamic cavitation a set number of times. The number of times will be defined by the number following "Pass."

TABLE 16

| A comparison of residual oocysts processed with multiple cycles of whipped cream dispenser hydrodynamic cavitation | | | | | | | |
|---|---|---|---|---|---|---|---|
| Hydrodynamic Cavitation | Total Oocysts per Sample (Average) | | | Percent reduction compared to starting material | | | |
| | E. maxima | E. tenella | E. acervulina | E. maxima | E. tenella | E. acervulina | Total |
| | Experiment 1 | | | | | | |
| Original material | $4.15 \times 10^2$ | $1.63 \times 10^2$ | $1.19 \times 10^3$ | — | — | — | — |
| Pass 1 | $2.88 \times 10^2$ | $9.8 \times 10^1$ | $8.7 \times 10^2$ | 31% | 40% | 30% | 31% |
| | Experiment 2 | | | | | | |
| Original material | $3.03 \times 10^2$ | $2.12 \times 10^2$ | $7.63 \times 10^2$ | — | — | — | — |
| Pass 1 | $2.05 \times 10^2$ | $1.14 \times 10^2$ | $6.14 \times 10^2$ | 32% | 46% | 20% | 27% |
| Pass 2 | $1.62 \times 10^2$ | $5.83 \times 10^1$ | $3.56 \times 10^2$ | 47% | 73% | 53% | 55% |
| Pass 3 | $1.70 \times 10^2$ | $6.65 \times 10^1$ | $4.35 \times 10^2$ | 44% | 69% | 43% | 47% |

Experiment 1 (see table 16) was performed to gauge the worth of pursuing a new cell disruption technique, and Experiment 2 was performed to further explore the technique. Ultimately, Experiment 1 showed comparable conversion of oocysts to sporocysts across all species that performed similarly to early tests with previously explored oocyst shearing techniques, such as shaking with glass beads. In Experiment 2 "Pass 2" demonstrated superior conversion to "Pass 1," while "Pass 3" showed comparable results to "Pass 2," indicating that increased exposure to nitrogen cavitation did not necessarily improve the conversion further.

Following the success of hydrodynamic cavitation under the limited parameters of the previously established EurKitchen approach, the protocol was refined further to incorporate a commercial grade hydrodynamic cell disruptor, the process for which is explored in greater detail in the sixth embodiment.

Further investigations were performed by using a cell disruption vessel (Parr™ 4639) with nitrogen gas supplied through a nitrogen filling connection (Parr™ 1831) at varying pressures, 1000 psi and 1500 psi, and then allowing the nitrogen gas to dissolve into the dilute vaccine for 5 minutes.

Although specifics are provided for pressure and time, it should be stated that the specifics of the process can occur across a broader range. This range can consist of pressures ranging from 500-5000 psi, time of exposures that last from 1-30 minutes and diluents that vary in composition. These compositions can consist of distilled water, phosphate buffered saline (PBS) and other variants of the two.

TABLE 17

| | Total Oocysts per Sample (Average) | | | Percent reduction compared to respective starting material | | | |
|---|---|---|---|---|---|---|---|
| Hydrodynamic Cavitation | Large | Medium | Small | Large | Medium | Small | Total Oocyst |
| Original material (1000 psi) | $2.22 \times 10^2$ | $1.12 \times 10^2$ | $4.06 \times 10^2$ | — | — | — | — |
| 1000 psi/5 min | $9.10 \times 10^1$ | $6.30 \times 10^1$ | $3.34 \times 10^2$ | 47% | 5% | 23% | 27% |
| Original material (1500 psi) | $2.59 \times 10^2$ | $1.54 \times 10^2$ | $4.48 \times 10^2$ | — | — | — | — |
| 1500 psi/5 min | $1.14 \times 10^2$ | $8.17 \times 10^1$ | $3.22 \times 10^2$ | 56% | 47% | 28% | 40% | in vitro comparison of residual oocysts processed by multiple pressures of cell disruption vessel hydrodynamic cavitation The liquid preparation was enumerated via the McMaster's floatation chamber method before and after being processed by hydrodynamic cavitation. The results showed that both tested pressures were able to convert approximately 50% and 25% of oocysts to sporocysts in the large and small species respectively. There was an increased conversion in the medium species at the higher tested pressure.

6.7.2. In Vivo Hydrodynamic Cavitation Studies (1st Method)

In this series of experiments, oocyst membrane disruption was completed using hydrodynamic cavitation and infectivity was evaluated via an oocyst output model. Enumeration of the remaining oocysts were calculated and shown below. Day of hatch chicks (15 per treatment) were inoculated with either oocysts or hydrodynamic cavitation-released sporocysts with residual oocysts via spray vaccination and intestinal contents were collected on day 7.

The data in Tables 18 & 19 below demonstrate the effectiveness of in vivo delivery of EurKitchen hydrodynamic cavitation-released sporocysts. The data in Table 19 was collected in a separate experiment from the data in Table 18.

TABLE 18

| | In vivo infectivity comparison of multiple cycles of artisan whipped cream dispenser hydrodynamic cavitation | | | | | |
|---|---|---|---|---|---|---|
| Hydrodynamic | Frequency of Response (Birds infected/Birds sprayed) | | | Amplitude of Response (Average oocyst output per bird) | | |
| Cavitation | E. maxima | E. tenella | E. acervulina | E. maxima | E. tenella | E. acervulina |
| Pass 1 | 6/15 (40%) | 8/15 (53%) | 9/15 (60%) | $5.77 \times 10^4$ | $1.44 \times 10^5$ | $1.35 \times 10^5$ |
| Pass 2 | 9/15 (60%) | 5/15 (33%) | 13/15 (87%) | $2.08 \times 10^4$ | $1.13 \times 10^3$ | $1.36 \times 10^4$ |
| Pass 3 | 6/15 (40%) | 4/15 (27%) | 12/15 (80%) | $8.23 \times 10^3$ | $1.45 \times 10^5$ | $3.00 \times 10^4$ |

TABLE 19

| | In vivo infectivity comparison of artisan whipped cream dispenser hydrodynamic cavitation | | | | | |
|---|---|---|---|---|---|---|
| Hydrodynamic | Frequency of Response (Birds infected/Birds sprayed) | | | Amplitude of Response (Average oocyst output per bird) | | |
| Cavitation | E. maxima | E. tenella | E. acervulina | E. maxima | E. tenella | E. acervulina |
| Oocysts | 10/12 (83%) | 10/12 (83%) | 12/12 (100%) | $5.23 \times 10^5$ | $6.84 \times 10^4$ | $3.71 \times 10^5$ |
| Pass 2 | 14/15 (93%) | 14/15 (93%) | 15/15 (100%) | $4.13 \times 10^5$ | $4.21 \times 10^5$ | $7.2.6 \times 10^5$ |
| Improvement | 10% | 10% | 0% | none | 6.2-fold | 2.0-fold |

No oocysts were observed in the intestinal contents of the untreated control birds. The eye drop control for this experiment yielded higher frequency and amplitude of response as compared to the experimental treatment groups. Table 18 demonstrated the comparative effectiveness of different "Pass" numbers and Table 19 demonstrated the effectiveness of the best performing, "Pass 2" compared to an oocyst eye spray delivery.

6.7.3. In Vivo Hydrodynamic Cavitation Studies (2nd Method)

The data in Tables 20 & 21 below demonstrate the effectiveness of the cell disruption process via cell disruption vessel hydrodynamic cavitation. The data in both Tables 20 & 21 were collected from the same experiment.

TABLE 20

| | in vivo infectivity comparison of cell disruption vessel hydrodynamic cavitation (1000 psi) | | | | | |
|---|---|---|---|---|---|---|
| Hydrodynamic | Frequency of Response (Birds infected/Birds sprayed) | | | Amplitude of Response (Average oocyst output per bird) | | |
| Cavitation | E. maxima | E. tenella | E. acervulina | E. maxima | E. tenella | E. acervulina |
| Oocysts | 7/15 (47%) | 5/15 (40%) | 15/15 (100%) | $8.42 \times 10^4$ | $5.09 \times 10^3$ | $8.10 \times 10^4$ |
| 1000 psi | 12/15 (80%) | 9/15 (60%) | 13/15 (87%) | $3.38 \times 10^5$ | $2.38 \times 10^5$ | $1.11 \times 10^5$ |
| Improvement | 33% | 20% | 0% | 4.0-fold | 46.6-fold | 1.4-fold |

TABLE 21

| In vivo infectivity comparison of cell disruption vessel hydrodynamic cavitation (1500 psi) | | | | | | |
|---|---|---|---|---|---|---|
| Hydrodynamic | Frequency of Response (Birds infected/Birds sprayed) | | | Amplitude of Response (Average oocyst output per bird) | | |
| Cavitation | E. maxima | E. tenella | E. acervulina | E. maxima | E. tenella | E. acervulina |
| Oocysts | 7/15 (47%) | 5/15 (40%) | 15/15 (100%) | $8.42 \times 10^4$ | $5.09 \times 10^3$ | $8.10 \times 10^4$ |
| 1500 psi | 11/15 (73%) | 10/15 (67%) | 15/15 (100%) | $8.27 \times 10^3$ | $1.69 \times 10^5$ | $4.35 \times 10^4$ |
| Improvement | 26% | 27% | 0% | none | 33.2-fold | none |

No oocysts were observed in the intestinal contents of the untreated control birds. The eye drop control for this experiment yielded higher frequency and amplitude of response as compared to the experimental treatment groups. The 1000 psi treatment demonstrated improved frequency of response for E. maxima and E. tenella and improved amplitude of response for all species. The 1500 psi treatment demonstrated improved frequency of response for E. maxima and E. tenella but the no impact on amplitude for E. maxima and E. acervulina however, there was a large increase in the amplitude response for E. tenella.

As expected, the refined hydrodynamic cavitation technique demonstrated by the cell disruption vessel outperformed the less controllable whipped cream dispenser approach. All species with the exception of E. acervulina showed improved infectivity, and in terms of E. tenella oocyst output, both cell disruption vessel pressure parameters showed demonstrable increases.

6.8. In Vitro Experiments with Additional Vaccines

In previous sections, methods were described for disrupting oocyst membranes to release sporocysts to improve vaccine performance. The initial testing was performed with a 1st broiler chicken coccidia vaccine in both manual and automated processes. Here, the process of disrupting oocyst membranes in a 2nd broiler chicken coccidia vaccine, a 1st and 2nd layer chicken coccidia vaccine and a 1st turkey coccidia vaccine are described.

For manual processing, vaccine was added to glass beads and vigorously shaken. The number of large, medium and small oocysts were counted and compared pre- and post-manual processing. In addition, an automated system was used, in which an aliquot of vaccine was added to a bead mill and samples processed. In this instance a disposable disperser system (IKA ULTRA-TURRAX Tube Drive system) was used, but any similar system would be expected to yield similar results.

For counting purposes, the oocysts included in the tested vaccines were classified as large, medium, and small based on their sizes as outlined in Conway and McKenzie (Poultry Coccidiosis: Diagnostic and Testing Procedures, 3rd Edition, June 2007, Wiley-Blackwell). Included in the set tested were the following Eimeria species: E. acervulina, E. adenoeids, E. brunetti, E. hagani, E. meleagrimitis E. mivati, E. maxima, E. necatrix, E. praecox, and E. tenella, from various commercial sources. The set included at least one species of both non-attenuated and attenuated (precocious) strains. Each sample was counted three times and the average listed below.

TABLE 22

| Oocyst reduction using a 1st layer chicken coccidia vaccine | | | | | | | |
|---|---|---|---|---|---|---|---|
| 1st Layer Chicken | Total Oocysts per Sample(Average) | | | Percent reduction compared to starting material | | | |
| Coccidia Vaccine | Large | Medium | Small | Large | Medium | Small | Total |
| Original material | $8.56 \times 10^1$ | $1.88 \times 10^2$ | $4.46 \times 10^2$ | — | — | — | — |
| Manual | $2.22 \times 10^1$ | $5.89 \times 10^1$ | $1.58 \times 10^2$ | 74% | 69% | 65% | 67% |
| Automated | $2.56 \times 10^1$ | $9.67 \times 10^1$ | $2.11 \times 10^2$ | 70% | 49% | 53% | 54% |

TABLE 23

| Oocyst reduction using a 2nd layer chicken coccidia vaccine | | | | | | | |
|---|---|---|---|---|---|---|---|
| 2nd Layer Chicken | Total Oocysts per Sample (Average) | | | Percent reduction compared to starting material | | | |
| Coccidia Vaccine | Large | Medium | Small | Large | Medium | Small | Total |
| Original material | $1.86 \times 10^2$ | $4.94 \times 10^1$ | $1.26 \times 10^3$ | — | — | — | — |
| Manual | $3.33 \times 10^1$ | $1.72 \times 10^2$ | $4.10 \times 10^2$ | 82% | 65% | 67% | 68% |
| Automated | $6.89 \times 10^1$ | $2.08 \times 10^1$ | $5.98 \times 10^2$ | 63% | 58% | 52% | 55% |

TABLE 24

| Oocyst reduction using a 2$^{nd}$ broiler chicken coccidia vaccine | | | | | | | |
| 2$^{nd}$ Broiler Chicken Coccidia Vaccine | Total Oocysts per Sample (Average) | | | Percent reduction compared to starting material | | | |
| | Large | Medium | Small | Large | Medium | Small | Total |
| Original material | $4.22 \times 10^2$ | $3.43 \times 10^2$ | $1.24 \times 10^3$ | — | — | — | — |
| Manual | $6.22 \times 10^2$ | $1.66 \times 10^2$ | $4.32 \times 10^2$ | 85% | 52% | 65% | 67% |
| Automated | $5.33 \times 10^1$ | $1.47 \times 10^1$ | $5.82 \times 10^2$ | 87% | 57% | 53% | 61% |

TABLE 25

| Oocyst reduction using a 1$^{st}$ turkey coccidia vaccine | | |
| 1$^{st}$ Turkey Coccidia Vaccine | Total Oocysts per Sample (Average) Medium* | Percent reduction compared to starting material Medium |
| Original material | $3.11 \times 10^2$ | |
| Manual | $1.12 \times 10^2$ | 64% |
| Automated | $1.20 \times 10^1$ | 61% |

*No large or small oocysts present in the vaccine.

Results indicate general susceptibility of oocysts to shearing for a wide variety of vaccines tested, indicating that the systems and processes described have broad applicability.

7. GENERALIZED STATEMENTS OF THE DISCLOSURE

The following numbered statements provide a general description of the disclosure and are not intended to limit the appended claims.

Statement 1: A method of vaccinating an animal against *Eimeria* comprising the steps of: providing a solution of *Eimeria* oocysts, the oocysts having an outer membrane and containing viable sporocysts therein; disrupting at least some of the *Eimeria* oocyst outer membranes which results in a modified solution; and delivering the modified solution to an animal.

Statement 2: A method of protecting an animal against an apicomplexan disorder comprising the steps of: providing a solution of apicomplexa oocysts, the oocysts having an outer membrane and containing viable sporocysts therein; disrupting at least some of the apicomplexa oocyst outer membranes which results in a modified solution; and delivering the modified solution to an animal.

Statement 3: The method of any of Statements 1-2, the viable sporocysts are released from the disrupted membrane.

Statement 4: The method of any of Statements 1-3, where the modified solution is delivered to an animal in at the time of disrupting the membranes.

Statement 5: The method of Statement 1-3, where the modified solution is delivered to the animal within 5 days of the disruption which results in the modified solution.

Statement 6: The method of any of Statements 1-5, where the modified solution is delivered by spray.

Statement 7: The method of any of Statements 1-6, where the *Eimeria* or apicomplexa oocysts are *Eimeria* oocysts of single *Eimeria* species or apicomplexa oocysts from a single apicomplexa species.

Statement 8: The method of any of Statements 1-6, where the *Eimeria* or apicomplexa oocysts are *Eimeria* oocysts from an *Eimeria* vaccine containing two or more *Eimeria* species or apicomplexa oocysts from two or more apicomplexa species.

Statement 9: The method of any of Statements 1-8, wherein the solution of *Eimeria* or apicomplexa oocysts is a concentrated vaccine solution.

Statement 10: The method of any of Statements 1-8, wherein the solution of *Eimeria* or apicomplexa oocysts is a diluted vaccine solution.

Statement 11: A system for disrupting an outer membrane of *Eimeria* oocysts, and delivering the resulting solution to an animal in real-time, the system comprising: a vessel containing *Eimeria* oocysts in a solution, the oocysts having an outer membrane and containing viable sporocysts therein; an oocyst processing chamber where the outer membrane of at least some of the *Eimeria* oocysts are disrupted which results in a modified solution; and a delivery outlet, whereby the modified solution is moved from the vessel through the processing chamber to the delivery outlet where the modified solution is delivered to an animal.

Statement 12: A system for disrupting an outer membrane of apicomplexa oocysts, and delivering the resulting solution to an animal in real-time, the system comprising: a vessel containing apicomplexa oocysts in a solution, the oocysts having an outer membrane and containing viable sporocysts therein; an oocyst processing chamber where the outer membrane of at least some of the apicomplexa oocysts are disrupted which results in a modified solution; and a delivery outlet, whereby the modified solution is moved from the vessel through the processing chamber to the delivery outlet where the modified solution is delivered to an animal.

Statement 13: The system of Statements 11-12, where the viable sporocysts are released from the disrupted membrane.

Statement 14: The system of any of Statements 11-13, wherein the oocyst processing chamber is at least one of a group consisting of: a high pressure homogenizer, a rotor stator mixer, a chamber vessel containing hard beads and an agitator attached thereto, a pair of vibrating plates, an ultrasonicator, hydrodynamic cavitation device, high pressure sprayer, or a combination thereof.

Statement 15: The system of any of Statements 11-14, wherein the homogenizer provides a pressure of about 3000 psi.

Statement 16: The system of any of Statements 11-15, wherein the number of *Eimeria* or apicomplexa oocysts ruptured is between about 5 and 50% for oocysts smaller than 20 microns on their longest dimension, between about 15 and 75% for oocysts ranging in size between 20 microns and 30 microns on their longest dimension, and between about 25 and 90% for oocysts larger than 30 microns on their longest dimension.

Statement 17: The system of any of Statements 11-16, wherein the solution containing the *Eimeria* or apicomplexa oocysts includes at least one proteolytic enzyme.

Statement 18: The system of Statement 17, where the proteolytic enzyme is trypsin, chymotrypsin or a mixture thereof.

Statement 19: The system of any of Statements 11-18, wherein the solution containing the *Eimeria* or apicomplexa oocysts is a concentrated vaccine solution.

Statement 20: The system of any of Statements 11-18, wherein the solution containing the *Eimeria* or apicomplexa oocysts further comprises an aqueous diluent which comprising buffer salts; sugars; proteins or protein hydrolysates; dyes; or thickeners.

Statement 21: A method of disrupting oocyst membranes at the time of delivery to an animal, the method comprising the steps of: providing a vessel for containing a volume of *Eimeria* oocysts in solution, the oocysts having an outer membrane and containing viable sporocysts therein; providing a system for disrupting the outer membrane of the oocyst; providing a delivery device; moving the solution from the first vessel into the system; passing the solution through the processing chamber, whereby at least some of the *Eimeria* oocyst membranes are disrupted which results in a modified solution; and moving the modified solution from the system to the delivery device where the modified solution is delivered to an animal.

Statement 22: A method of disrupting oocyst membranes at the time of delivery to an animal, the method comprising the steps of: providing a vessel for containing a volume of apicomplexa oocysts in solution, the oocysts having an outer membrane and containing viable sporocysts therein; providing a system for disrupting the outer membrane of the oocyst; providing a delivery device; moving the solution from the first vessel into the system; passing the solution through the processing chamber, whereby at least some of the apicomplexa oocyst membranes are disrupted which results in a modified solution; and moving the modified solution from the system to the delivery device where the modified solution is delivered to an animal.

Statement 23: The method of any of Statements 21-22, wherein the system comprises at least one from the group consisting of a high-pressure homogenizer, an ultrasonicator, a rotor stator mixer, a vessel containing hard beads therein and an agitator attached thereto, a pair of vibrating plates, a hydrodynamic cavitation device, a high pressure sprayer, or a combination thereof.

Statement 24: The method of any of Statements 21-23, wherein the homogenizer provides a pressure of greater than about 3000 psi.

Statement 25: The method of any of Statements 21-24, wherein the number of oocysts ruptured is at least about 5% for oocysts smaller than 20 microns on their longest dimension, at least about 15% for oocysts ranging in size between 20 microns and 30 microns on their longest dimension, and at least about 25% for oocysts larger than 30 microns on their longest dimension.

Statement 26: The method of any of Statements 21-25, wherein the solution of *Eimeria* oocysts or apicomplexa is a concentrated vaccine solution.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world. It is to be understood that, while the disclosure has been described in conjunction with the detailed description, thereof, the foregoing description is intended to illustrate and not limit the scope. Other aspects, advantages, and modifications are within the scope of the claims set forth below. All publications, patents, and patent applications cited in this specification are herein incorporated by reference as if each individual publication or patent application were specifically and individually indicated to be incorporated by reference.

What is claimed is:

1. A system for disrupting outer membranes of *Eimeria* oocysts and delivering the resulting solution to an animal in real-time, the system comprising:
   a vessel containing *Eimeria* oocysts in a solution, the oocysts having an outer membrane and containing viable sporocysts therein;
   an oocyst processing chamber that receives the solution from the vessel and that is configured to modify the solution by disrupting the outer membranes of some of the *Eimeria* oocysts which results in viable sporocysts being released from the disrupted oocysts; and
   a delivery outlet proximate to the oocyst processing chamber and configured to receive the modified solution from the processing chamber, and deliver the modified solution to an animal within a 24 hour period of time after disrupting the outer membranes in the oocyst processing chamber.

2. The system of claim 1, wherein the modified solution is delivered to the animal within the 24 hour period of time while at room temperature after disrupting the outer membranes in the oocyst processing chamber.

3. The system of claim 1, wherein the oocyst processing chamber is at least one of a group of: a rotor stator mixer, a chamber vessel containing a plurality of agitators and a spinner attached thereto, a pair of vibrating plates, an ultrasonicator, or a combination thereof.

4. The system of claim 3, wherein the agitators are cylindrical in shape.

5. The system of claim 1, wherein the number of *Eimeria* oocysts ruptured is between about 5 and 50% for *Eimeria* oocysts smaller than 20 microns on their longest dimension, between about 15 and 75% for *Eimeria* oocysts ranging in size between 20 microns and 30 microns on their longest dimension, and between about 25 and 90% for *Eimeria* oocysts larger than 30 microns on their longest dimension.

6. The system of claim 3, wherein the spinner causes the chamber vessel to spin, vibrate or shake when activated.

7. The system of claim 1, wherein the solution containing the *Eimeria* oocysts includes at least one proteolytic enzyme, where the at least one proteolytic enzyme is trypsin, chymotrypsin or a mixture thereof.

8. The system of claim 1, wherein the solution containing the *Eimeria* oocysts is a concentrated vaccine solution.

9. The system of claim 1, wherein the solution containing the *Eimeria* oocysts further comprises an aqueous diluent which comprises buffer salts; sugars; proteins or protein hydrolysates; dyes; or thickeners.

10. A method of disrupting oocyst membranes at the time of delivery to the mucosa of an animal, the method comprising:

providing a vessel for containing a volume of oocysts in solution, the oocysts having an outer membrane and containing viable sporocysts therein;

providing an inline system for disrupting the outer membrane of some of the oocysts;

providing a delivery device proximate to the system;

moving the solution from the vessel into the system;

passing the solution through the system, whereby at least some of the oocyst membranes are disrupted which results in a release of the viable sporocysts from the oocysts, wherein a modified solution includes the released viable sporocysts; and moving the modified solution from the system to the delivery device where the modified solution is delivered to the mucosa of an animal within a 24 hour period of time after disrupting the outer membranes in the system.

11. The method of claim 10 wherein the system comprises at least one from the group of an ultrasonicator, a rotor stator mixer, a pair of vibrating plates, a at least two cylindrical agitators, a spinner or a combination thereof.

12. The method of claim 11 wherein the spinner enables the vessel to vibrate or shake when activated.

13. The method of claim 10 further comprising activating agitators to disrupt the outer membranes of the oocysts.

14. The method of claim 13, wherein the agitators comprise: vibrating plates comprising a first plate positioned on top of a second plate and disrupts the oocysts in the solution from the vessel when the solution from the vessel is passed in an area disposed between the first and second plates.

15. The method of claim 13, wherein the agitators are configured to disrupt the oocysts in the solution from the vessel so that the modified solution comprises a composition such that the number of oocysts whose outer membranes are ruptured is between about 5 and 50% for oocysts smaller than 20 microns on their longest dimension, between about 15 and 75% for oocysts ranging in size between 20 microns and 30 microns on their longest dimension, and between about 25 and 90% for oocysts larger than 30 microns on their longest dimension.

16. The method of claim 12, wherein the modified solution is delivered to the animal within the 24 hour period of time while at room temperature after disrupting the outer membranes in an oocyst processing chamber.

17. A system for disrupting outer membranes of oocysts and delivering a resulting solution to an animal in real-time, the system comprising:

an oocyst processing chamber comprising agitators to disrupt the outer membranes of the oocysts, including cell walls and cell membranes, and release viable sporocysts being from the disrupted oocysts;

a delivery outlet connected to the oocyst processing chamber and configured to: receive the released viable sporocysts from the processing chamber and then deliver the released viable sporocysts to an animal within a 24 hour period of time after the sporocysts are released.

18. The system of claim 17, wherein the agitators comprising either: (1) vibrating plates comprising a first plate positioned adjacent to a second plate and is configured to disrupt the outer membranes of the oocysts when the oocysts are passed in an area disposed between the first and second plates or (2) cylindrical agitators that are configured to disrupt the outer membranes of the oocysts by crushing or smashing.

19. The method of claim 11, wherein the vibrating plates are configured to disrupt the oocysts so that a disrupted oocysts solution comprises a composition such that the number of *Eimeria* oocysts whose outer membranes are ruptured is between about 5 and 50% for *Eimeria* oocysts smaller than 20 microns on their longest dimension, between about 15 and 75% for *Eimeria* oocysts ranging in size between 20 microns and 30 microns on their longest dimension, and between about 25 and 90% for *Eimeria* oocysts larger than 30 microns on their longest dimension.

20. A method of disrupting cells, the method comprising using the system of claim 18 to disrupt the outer membranes of *Eimeria* oocysts, including cell walls and cell membranes, and releasing viable sporocysts from the disrupted oocysts.

*    *    *    *    *